US006734344B2

(12) United States Patent
Laroche et al.

(10) Patent No.: US 6,734,344 B2
(45) Date of Patent: May 11, 2004

(54) *CONIOTHYRIUM MINITANS* β-(1,3) EXOGLUCANASE GENE *CBEG 1*

(75) Inventors: André J. Laroche, Lethbridge (CA); Timothy Yikai Huang, Lethbridge (CA); Michele M. Frick, Lethbridge (CA); Zhen-Xiang Lu, Lethbridge (CA); Hung Chang Huang, Lethbridge (CA); Kuo Joan Cheng, Richmond (CA)

(73) Assignee: Her Majesty the Queen in right of Canada, as represented by the Minister of Agriculture and Agrifood, Lethbridge (CA)

( * ) Notice: Subject to any disclaimer, the term of this patent is extended or adjusted under 35 U.S.C. 154(b) by 0 days.

(21) Appl. No.: 09/733,643

(22) Filed: Dec. 8, 2000

(65) Prior Publication Data

US 2003/0115627 A1 Jun. 19, 2003

Related U.S. Application Data

(60) Provisional application No. 60/170,168, filed on Dec. 10, 1999.

(51) Int. Cl.$^7$ .................. C12N 15/56; C12N 15/82; C12N 15/83; C12N 15/84; C12N 15/31

(52) U.S. Cl. ............. 800/288; 435/320.1; 435/419; 435/468; 435/252.3; 435/200; 536/23.2; 536/23.74; 800/293; 800/294

(58) Field of Search ................ 536/23.1, 23.2, 536/23.74; 435/320.1, 252.3, 419.2, 468, 469, 470; 800/278, 293, 294, 288

(56) References Cited

FOREIGN PATENT DOCUMENTS

| WO | WO 99/02662 | 1/1999 |
|----|-------------|--------|
| WO | WO 00/18909 | 6/2000 |

OTHER PUBLICATIONS

Reeck et al. 1987, "Homology" in proteins and nucleic acids: A terminology muddle and a way out of it. Cell 50:667.*
Zhu et al. 1994, Enhanced protection against fungal attack by constitutive co–expression of chitanase and glucanase genes in transgenic tobacco.

OTHER PUBLICATIONS

Borgia, P.T. and Dodge, C.L. (1992) Characterization of *Aspergillus nidulans* mutants deficient in cell wall chitin or glucan. J. Bacteriol. 174(2):377–383.

Breen, J.P. and Crouch, M.L. (1992) Molecular analysis of a Cruciferin storage protein gene family of *Brassica napus*. Plant Mol. Biol. 19:1049–1055.

Chen, H., Li, X.-L. and Ljungdahl, L.G. (1997) Sequencing of a 1,3–1,4–β–D–glucanase (lichenase) from the anaerobic fungus Orpinomyces strain PC–2: Properties of the enzyme expressed in *Escherichia coli* and evidence that the gene has a bacterial origin. J. Bacteriol. 179(19):6028–6034.

Chesson, A., Forsberg, C.W. and Grenet, E. (1995) Improving the digestion of plant cell walls and fibrous feeds. In: Recent IVth developments in the nutrition of herbivores, M. Journet, E. Grenet, M.–H. Farce, M. Theriez, C. Demarquilly (eds). Proceedings of the international symposium on the nutrition of herbivores, pp. 249–277. INRA Editions, Paris.

Cho, M.-J., Jiang, W. and Lemaux, P.G. (1998) Transformation of recalcitrant barley cultivars through improvement of regenerability and decreased albinism. Plant Science 138:229–244.

Cohen–Kupiec, R., Broglie, K.E., Friesem, D., Broglie, R.M. and Chet, I. (1999) Molecular characterization of a novel beta–1,3–exoglucanase related to mycoparasitism of *Trichoderma harzianum*. Gene 226:147–154.

Copa–Patino, J.L., Reyes, F. and Perez–Leblic, M.I. (1989) Purification and properties of a 1,3–β–glucanase from *Penicillium oxalicum* autolysates. FEMS Microbiol. Lett. 65:285–292.

de la Cruz, J., Pintor–Toro, J.A., Benitez, T., LIobell, A. and Romero, L.C. (1995) A novel endo–beta–1,3–glucanase, BGN13.1, involved in the mycoparasitism of *Trichoderma harzianum*. J. Bacteriol. 177(23):6937–6945.

Depicker, A., Stachel, S., Dhaese, P., Zambryski, P. and Goodman, H.M. (1982) Nopaline synthase: transcript mapping and DNA sequence *Agrobacterium tumefaciens*. J. Mol. Appl. Genet. 1(6):561–573.

Erickson, F.L., Holzberg, S., Calderon–Urrea, A., Handley, V., Axtell, M., Corr, C. and Baker, B. (1999) The helicase domain of the TMV replicase proteins induces the N–mediated defence response in tobacco. Plant J. 18(1):67–75.

Fling, M.E., Kopf, J. and Richards, C. (1985) Nucleotide sequence of the rtransposon Tn7 gene encoding an aminoglucoside–modifying enzyme 3''(9)–O–nucleotidyltransferase. Nucleic Acids Res. 13(19):7095–7106.

Fraley, R.T., Rogers, S.G., Horsch, R.B., Sanders, P.R. and Flick, J.S. (1983) Expression of bacterial genes in plant cells *Agrobacterium tumefaciens*. Proc. Natl. Acad. Sci. USA 80:4803–4807.

Fraley, R.T., Rogers, S.G., Horsch, R.B., Eichholtz, D.A., Flick, J.S, Fink, C.L., Hoffman, N.L. and Sanders, P.R. (1985) The SEV system: a new disarmed Ti plasmid vector system for plant transformation. Bio/Technology 3:629–635.

GenBank Accession No. AJ002397 (Feb. 6, 1999) *Trichoderma harzianum* gene coding beta–1,3 exoglucanase.

GenBank Accession No. AF253421 (Jul. 1, 200) *Trichoderma atroviride* glucan 1,3–beta–glucosidase GLUC78 precursor, gene, complete cds.

GenBank Accession No. AF247649 (Feb. 13, 2001) *Coniothyrium minitans* beta–1,3–glucanase (cmg1) mRNA, complete cds.

GenBank Accession No. M63657 (Aug. 20, 1993) Bacteriophage K1F endo–N–acylneuraminidase gene, complete cds.

GenBank Accession No. X72292 (Sep. 24, 1999) *A.thaliana* (clone GBGa483) mRNA for exopolygalacturonase.

GenBank Accession No. X84085 (Apr. 30, 1996) *T.harzianum* mRNA for endo–1,3(4)–beta–glucanase.

GenBank Accession No. AF029354 (Apr. 2, 1998) *Ampelomyces quisqualis* exo–beta–1,3–glucanase (exgA) mRNA, complete cds.

GenBank Accession No. L48994 (Jan. 13, 2000) *Cochliobolus carbonum* exo–beta 1,3 glucanase (EXG1) gene, complete cds.

GenBank Accession No. AF099800 (Jan. 14, 1999) *Azotobacter vinelandii* mannuronan C–5–epimerase AlgE7(algE7) gene, complete cds.

GenBank Accession No. M14782 (Apr. 28, 1993) *Bacillus phage phi–29* head morphogenesis, major head protein, head fiber protein, tail protein, upper collar protein, lower collar protein, pre–neck appendage protein, morphogenesis (13), lysis, morphogenesis (15), encapsidation genes, complete cds.

Gielen, J., De Beuckeleer, M., Seurinck, J., Deboeck, F. and De Greve, H. (1984) The complete nucleotide sequence of the TL–DNA of the *Agrobacterium tumefaciens* plasmid pTiAch5. EMBO J. 3(4):835–846.

Hajdukiewicz, P., Svab, A. and Maliga, P. (1994) The small, versatile pPZP family of Agrobacterium binary vectors for plant transformation. Plant Mol. Biol. 25:989–994.

Henrissat, B. Claeyssens, M., Tomme, P., Lemesle, L. and Mornon, J.–P. (1989) Cellulase families revealed by hydrophobic cluster analysis. Gene 81:83–95.

Henrissat, B. and Bairoch, A. (1993) New families in the classification of glycosyl hydrolases based on amino acid sequence similarities. Biochem. J. 293:781–788.

Hoj, P.B. and Fincher, G.B. (1995) Molecular evolution of plant β–glucan endohydrolases. Plant J. 7(3):367–379.

Huang, H.C. and Hoes, J.A. (1976) Penetration and infection of *Sclerotinia sclerotiorum* by *Coniothyrium minitans*. Can. J. Bot. 54: 406–410.

Huang, H.C. and Kokko, E.G. (1987) Ultrastructure of hyperparasitism of *Coniothyrium minitans* on sclerotia of *Sclerotinia sclerotiorum*. Can. J. Bot. 65:2483–2489.

Huang, H.C. and Kokko, E.G. (1988) Penetration of hyphae of *Sclerotinia sclerotiorum* by *Coniothyrium minitans* without the formation of appressoria. Phytopath. Zeit. 123:133–139.

Jones, D., Gordon, A.H. and Bacon, J.S.D. (1974) Co–operative action by endo– and exo–β–(1,3)–glucanases from parasitic fungi in the dedgradation of cell–wall glucans of *Sclerotinia sclerotiorum* (Lib.) de Bary. Biochem. J. 140:47–55.

Kay, R., Chan, A., Daly, M. and McPherson, J. (1987) Duplication of CaMV 35S orimoter sequences created a strong enhancer to plant genes. Science 236:1299–1302.

McElroy, D., Blowers, A.D., Jenes, B. and Wu, R. (1991) Construction of expression vectors based on the rice actin 1 (Act1) 5' region for use in monocot transformation. Mol. Gen. Genet. 231:150–160.

Miller, G.L. (1959) Use of dinitrosalicyclic acid reagent for determination of reducing sugars. Anal. Chem. 31(3):426–428.

Moloney, M.M., Walker, J.M. and Sharma, K.K. (1989) High efficiency transformation of *Brassica napus* using Agrobacterium vectors. Plant Cell Reports 8: 238–242.

Nielsen, H., J. Engelbrecht, S. Brunak, and G. V. Heijne. (1997) Identification of prokaryotic and eukaryotic signal peptides and prediction of their cleavage sites. Prot. Eng. 10(1): 1–6.

Odell, J.T., Nagy, F. and Chua, N.-H. (1985) Identification of DNA sequences required for activity of the cauliflower mosaic virus 35S promoter. Nature 313: 810–812.

Peberdy, J.F. (1990) Fungal cell wall—a review. In: Biochemistry of cell walls and membranes in fungi, P.J. Kuhn, A.P.J. Trinci, M.J. Jung, M.W. Goosey and L.G. Cooping (eds.), pp. 5–30.

Petter J.G., and Vimr, E.R. (1993) Complete nucleotide sequence of the bacteriophage K1F tail gene encoding endo–N–acylneuraminidase (endo–N) and comparison to an endo–N homolog in bacteriophage PK1E. J. Bacteriol. 175(14):4354–4363.

Schaeffer, H.J., Leykam, J. and Walton, J.D. (1994) Cloning and targeted gene disruption of EXG1, encoding exo–beta 1,3–glucanase, in the phytopathogenic fungus *Cochliobolus carbonum*. Appl. Environ. Microbiol. 60(2):594–598.

Scofield, S.R. and Crouch, M.L. (1987) Nucleotide sequence of a member of the napin storage protein family from *Brassica napus*. J. Biochem. 262(25):12202–12208.

Stahmann, K.-P., Schimz, K.-L. and Sahm, H. (1993) Purification and characterization of four extracellular 1,3–β–glucanases of *Botrytis cinerea*. J. Gen. Microbiol. 139:2833–2840.

Stalker, D.M., Thomas, C.M. and Helinski, D.R. (1981) Nucleotide sequence of the region of the origin of replication of the broad host range plasmid RK2. Mol. Gen. Genet. 181:8–12.

Svanem, B.I.G., Skjaak–Braek, G., Ertesvaag, H. and Valla, S. (1999) Cloning and expression of three new *Azotobacter vinelandii* genes closely related to a previously described gene family encoding mannuronan C–5–epimerases. J. Bacteriol. 181(1):68–77.

Teather, R.M. and Erfle, J.D. (1990) DNA sequence of a *Fibrobacter succinogenes* mixed–linkage beta–glucanase (1,3–1,4–beta–D–glucan 4–glucanohydrolase) gene. J. Bacteriol. 172(7):3837–3841.

Thomson, J.A. (1993) Molecular biology of xylan degradation. FEMS Microbiol. Rev. 104:65–82.

Tingay, S., McElroy, D., Kalla, R., Fieg, S., Wang, M., Thornton, S. and Brettell, R. (1997) *Agrobacterium tumefaciens*–mediated barley transformation. Plant J. 11(6):1369–1376.

Torki, M., Mandaron, P., Thomas, F., Quigley, F., Mache, R. and Falconet, D. (1999) Differential expression of a polygalacturonase gene family in *Arabidopsis thaliana*. Mol. Gen. Genet. 261(6):948–952.

Trick, H.N. and Finer, J. J. (1997) SAAT: sonication–assisted Agrobacterium–mediated transformation. Transgenic Res. 6:329–336.

Umemoto, N., Kakitani, M., Iwamatsu, A., Yoshikawa, M., Yamaoka, N. and Ishida, I. (1997) The structure and function of a soybean β–glucan–elicitor–binding protein. Proc. Natl. Acad. Sci. 94:1029–1034.

Vazquez–Garciduenas, S., Leal–Morales, C.A. and Herrera–Estella, A. (1998) Analysis of the β–1,3–glucanolytic system of the biocontrol . agent *Trichoderma hazarium*. Appl. Environ. Microbiol. 64(4):1442–1446.

Vlcek, C. and Paces,V. (1986) Nucleotide sequence of the late region of Bacillus phage phi–29 completes the 19285–bp sequence of phi–29 genome: comparison with the homologous sequence of phage PZA. Gene 46:215–225.

Wan, Y. and Lemaux, P.G. (1994) Generation of large numbers of independently transformed fertile barley plants. Plant Physiol. 104:37–48.

Weeks, J.T., Anderson, O.D. and Blechl, A.E. (1993) Rapid production of multiple independent lines of fertile transgenic wheat ( *Tricicum aestivum*). Plant Physiol. 102:1077–1084.

White, J., Chang, S.Y., Bibb, M.J. and Bibb, M.J. (1990) A cassette containing the bar gene of *Streptomyces hygroscopious*: a selectable marker for plant transformation. Nucleic Acids Res. 18(4):1062.

Wolf, M., Geczi, A., Simon, O. and Borriss, R. (1995) Genes encoding xylan and beta–glucan hydrolysing enzymes in *Bacillus subtilis*: characterization, mapping and construction of strains deficient in lichenase, cellulase and xylanase. Microbiology 141(2):281–290.

* cited by examiner i) Forward primer:
Alignment:

| aa: | K | G | D | G | V | T | D | D | T | A |
|---|---|---|---|---|---|---|---|---|---|---|
| 1. 5' | AAG | GGC | GAC | GGC | GTT | ACC | GAT | GAC | ACC | GCT 3' |
| 2. | | GGT | GAC | GGT | GTC | ACT | GAC | GAC | | |
| 3. | | GGT | GAT | GGT | GTT | ACC | GAC | GAC | ACG | |

Semi-degenerate primer Gf1:
```
       5' GGT GAT GGT GTT ACT GAT GA 3'
              C   C   C   C   C
```

FIG. 1A ii) Reverse primer:
Alignment:

| aa: | R | Q | I/V | R | N | F | V |
|---|---|---|---|---|---|---|---|
| 1. 5' | CGC | CAG | ATT | CGC | AAC | TTC | GTC 3' |
| 2. | CGC | CAA | ATC | CGC | AAC | TTG | |
| 3. | CGG | CAA | GTC | CGC | AAC | TTT | AAG |

Consensus sequence:
```
       5' CGC CAA ATT CGC AAC TT 3'
           G  G   C
```

Reverse semi-degenerate primer Gr1:
```
       3' GCG GTT TAA GCG TTG AA 5'
           C  C   G
```

FIG. 1B

```
Cbeg1     MRLLSFFSCLLAAGGPASALALPSPIANDATSAPLEERQ------ASSYWLENIQHQGRAA      55
Exg1      MRFSSLLACLGAVGIQAAAIPFQRRVDNTTDSGSLDAAQAAAAIVDGYWLNDLSGKGRAP      60
ExgA      MLAFSAGAFLLTLRVFLTATPSAAAPVAQAVEVPQAGAS-------GYWFGNIKRQGIAP      53
Trexo     -MGFIRSAVLSALTFAAACRGLATPGSEAEPSVEKRASS--------YWYENIAHQGIAP      51
Bgn13.1   --MLKLTALVALLLGAASATPTPSPPASDE-GITKRATS---------FYYPNMDHVN-AP     48

Cbeg1     FNANPAGYKVFRNVKDYGAKGDGVTDDSAAINAAIADGNRCAPWVCDSSTDTPAIVYFPS    115
Exg1      FNSNPN-YKVFRNVKDYGAKGDGVTDDSDAFNRAISDGSRCGPWVCDSSTDSPAVVYVPS    119
ExgA      YNENPAAYKVFRNVKLLGAKGDGVTDDTAAINAAIADGNRCG-QGCDSTTTSPAIIYFPA    112
Trexo     F--APSNYTVFRNVKDYGAKGDGVTDDTAAINNAILSGGRCG-RLCTSSTLTPAVVYFPA    108
Bgn13.1   RGFAPD-LDGDFNYPIYQTVNAG--DGNALQNAITTDGKGGS-RHPQWFASQPRVVYIPP    104

Cbeg1     GTYVIGKPIIMYYMTQLHGNPNNRPVLKASPNLRAIALALIDASPYQ--DGTGKPGWTSTNV    173
Exg1      GTYLINKPIIFYYMTALIGNPRELPVLKAASSLQALALIDGSPYS--NQNGEPGWISTNL    177
ExgA      GTYLISEPIIQYYYTQFVGDATNPPTLKAKDTFEGMGLIDADPYIP-GGDGANWYTNQNN    171
Trexo     GTYVISTPIIDQYYTNIIGDPTNLPTIKATAGFSGIALIDGDTYYGDNNPNDPNWISTNV    168
Bgn13.1   GTYTISKTLRFNTDTILMGDPTNPPIIKAAAGFSGDQTLISAQDP---STNEKGELS-      158

Cbeg1     FTRQIRNFVIDLTPIPATS-GAQGIHWPASQATSIQDVKIQMNVAANSV-HVGIFIENGS    231
Exg1      FLRQIRNLIIDGTAVAPTS-GFQAIHWPASQATSIQNVKIRMTQASNSV-HAGIFVENGS    235
ExgA      FYRQIRNFVIDIKDTKAAA----GIHWQVSQATSLQNIRFEMATGEAGANQKGIFQDNGS    227
Trexo     FYRQVRNFKLDMTSIPTSAPKIYGIHWPTAQATSLQNIQITMSTASGNS-QVGLFIENGS    227
Bgn13.1   FAVAIKNVVLDTTAIPGGN-SFTALWGVAQAAHLQNVRITMSSSSGGNGHTGIRMGRGS    217

Cbeg1     GGHLTDIETVGGLHGLNVG-NQQFTMKNIVISNAVVGINQIWNWGWLMKGLTISDCSTAA    290
Eexg1     GGHMADLDITGGLYGMNIG-NQQFTMRNVKISKAVVGISQIWNWGWLYSGLQISDCGTAF    294
ExgA      GGFMSDLVFNGGAIGAFLG-SQQFTTRNMTFNNCGTAIFMNWNWLWTLKSIFNDCKLGL    286
Trexo     AGFLTDMTFNGGLIGAAIG-NQQYTMRNLVFNNCAQPLSAASIGSGFTRAISINNCGLGI    286
Bgn13.1   TLGLADVRVERGQNGIWIDGHQQASFHNIYFFQNTIGMLISSGNTFSIFSSTFDTCGTAF    277
```

FIG. 2A

```
Cbeg1    FSMKSLKDNSPDQNVASVIIDSTITNCPIFVDSAWTRTSTAAGSGQLILENIALNNVPV   350
Exg1     SMVNGG--SAGKQEVGSAVIIDSEITNCQKFVDSAWSQTSNPTGSGQLVIENIKLTNVPA   352
ExgA     DMANSP----DNQTVGSVLLLDSKFTNTPIGINSSFTQDSVPHTGGTLIIDNVDFEGSNV   342
Trexo    DMTAAE--------SITLIDSSISGTPVGIKTSFRRNQSPATSNSLIVENLSLNNVPV    336
Bgn13.1  PTLAGS---------PWIALIDAKSINS----GVTFTTNQFPS----FMIENLTKDN-GT   319

Cbeg1    AVKGPSG-TVLAGGTTTIAGWGQGNQYTP--GGPTKFQGAIT--PVRPAGLLDGKNFYAK   405
Exg1     AVVSNGA-TVLAGGSLTIQTWGQGNKYAPNASGPSKFQGAISG-ATRPTGLLQNGKFYSK   410
ExgA     AVQNVAGETLLAGKSK-VATWAQGNAMAAGQAQAGRVQGDVNNPPTKPQSLLGENGWFER   401
Trexo    AIQSSSGSTILAGGTTTIAAWGQGHQYTP--NGPTTFQGSITP-NSRPSSLLSGSNYYTR   393
Bgn13.1  PVVVVRG-STLVGASSHVNTYSYGNTVGR---NPT--YGDVTSSNTRPSALAPGGRYPYV   373

Cbeg1    SKPQYETVAVGNFVSARTSGAKG-------DGSTDDTTALQNAINSVASSGKILFLDHGHY   459
Exg1     SKPQYETLSTSSFISARGAGATG-------DGVTDDTRAVQAAVTQAASQNKVLFFEHGVY   464
ExgA     SKPQYENIDVSKFVSLKDAGAVG-------DGVTDDTAMIQKAIDGLQD-GQILHADHGAY   454
Trexo    SKPQYETLPVSSFRSVRSAGATG-------NAVTDDTAALQSVINSATACGQIVYFDAGIY   447
Bgn13.1  APPTYGDLPISSFLNVKDPAQNGNRQVKGDNTINEADTLNAILELAASQNKVAYFPFGKY   433

Cbeg1    KITKTLYLPPGT--KIVGETYPIILASGSTWNSKTNPVPVVQVGK-AGESGSVELSDFLI   516
Exg1     KVTNTIYVPPGS--RMVGEIFSAIMGSGSTFGDQANPVPIIQIGK-PGESGSIEWSDMIV   521
ExgA     LITKTIEIPAEKNIKIVGEIYTMFFITGKFFGNMDDPQPGFRVGKKSGDKGTFEMSDAII   514
Trexo    RITSTLSIPPGA--KIVGEEYPIIMSSGSFFNDQSNPKPVVQVGT-PGQTGQVEWSDMIV   504
Bgn13.1  RVDSTLFIPKGS--RIVGEAWATITGNGNFFKNENSPQPVVSVGR-AGDVGIAQLQDLRV   490

Cbeg1    GTQGPTPGAKLIEYNMATTKG--SGMWDVHTRIGGAKGTNLQVAQCP-----VGSVNDAC   569
Exg1     QTQGATPGAIVIQYNLNTALG--SGLWDVHTRIGGAKGTNLQVAQCPA---VLGQVKPEC   576
ExgA     STQGPAPGGILMEWNINAEAGK-AGLWDVHFRVGGFAGTNLQSSNCKKNPDTEHPPNEEC   573
Trexo    STQGTQAGAVLIEWNLATSGTP-SGMWDVHTRIGGFKGSNLQVAQCPVTA-SSTTVNTAC   562
Bgn13.1  TTNDVLPGAILVQFNMAGNNPGDVALWNSLVTVGGTRGAQALANACTN------NSNEC   543
```

FIG. 2B

```
Cbeg1   MAAHTNVHITKSANNVYMENNWFWTADHDLDDSVSTQISIFVGRGLLVEGTN--IWLYGN       627
Exg1    FSAHTNVHVTKGANGAYFENNWFWTADHDLDDADSTRINIYTGRGFHVEANN--VWIWAN       634
ExgA    IGSFMQLHITKSSS-GYFENVWLWTADHELDQPDHAQIDIYNGRGMLVESQG-PVWLVGT       631
Trexo   IGAYMSMHITASASNLYMENNWLWTADHDIDDSSNTQITIFSGRGLYVESTAGTFWFVGT       622
Bgn13.1 KGAFIGIHVAKGSS-PYIQNVWELGLRDHIAENFSGGTSHRRERWNFGPIRRNATCLYPI       602

Cbeg1   GAEHQSLYQYQFANAKDVFAGFIQSETPYYM--PTPDAKSQPYPVNS-ALNDPDYNTICP       684
Exg1    GAEHHTMYQYQFNAAQDIFAGYIQTETPYFQ--PTPIAP-LPYVSSS-KYSDPVYSSSQ-       689
ExgA    ASEHSQLSQYQFQGAKDIWYGAIQTETPYYQ--PNPKAN-VPFKKND-KFSDPDMSNTT-       686
Trexo   AVEHHTLYQYQFANTQNIYAGVIQTETPYYQ--PNPDAP-TPFNVNT-ALNDPNFATSCS       678
Bgn13.1 GSGHWWLYQLNLHNAANVVVSLLQAETNYHQGANTQQIPPAPWVANVGTWGDPDFSWCNG       662

Cbeg1   --SGQRCDALGLRVLNS-SNVLLYGEGFYSFFISNN--NSCSKNTN--SVRDCQNRMVSI       737
Exg1    -----TSAWGLRLLDA-KNVLIYGGGLYSFFDNYD--VGCSSPTAPNGFRDCQTRILSI       740
ExgA    ------SAWAVRIIDS-SSIWNYGAGTYSFFDNYS--QKCVVGQN------CQEHINEI       730
Trexo   GSSGRCAEAWGLRIVSS-QNILIYAAGLYSFFENNDGNTGCDVALGP--E-NCQNNIFDL       734
Bgn13.1 --GDKRCRMGPANFINGGSNIYTYASAAWAFFSGPG--QGCAQFEC------QQTIHWI       711

Cbeg1   EGS-STVRAYSLNEVGALQMLTVDGVDKADWMPNLSGYANTIG--YFSYNI--------       785
Exg1    EGS-TSVQAFGFSEVGVEWMVTAAGQDKANWKDNLSVYPTTIG--YLSYGF--------       788
ExgA    ENS-RNVNIFGLSTKASVNMISSGGVGLLKDEDNRSNFCATLG--IFAQA---------       777
Trexo   EGTLTNINVYNLGTVGVVNQITQNGNVLATSSSNVNAFADVIA--LFRLASGSGVTPPP       792
Bgn13.1 ASTPSNLQAFGLCSKDSVNTLRLGDGTFINTQNGYTGGWTPGGGDVARYTT--------       762

Cbeg1   ---------------------------------------------------------
Exg1    ---------------------------------------------------------
ExgA    ---------------------------------------------------------
Trexo   SSTTKAQSTTFSTIITSSPPKQTGWNFLGCYSDNVNGRTLANQVQVAGGASAMSIEACET      852
Bgn13.1 ---------------------------------------------------------
```

FIG. 2C

```
Cbeg1   -------------------------------------------------------
Exg1    -------------------------------------------------------
ExgA    -------------------------------------------------------
Trexo   ASESAGYTIAGVEYSGECWCDTKFQNGGGPASDGSAQCTMTCSGAPQETCGGPNRLDVYS   912
Bgn13.1 -------------------------------------------------------

Cbeg1   -------------------------------------------------------
Exg1    -------------------------------------------------------
ExgA    -------------------------------------------------------
Trexo   LATATGSASPPAATGWNFRGCYTDSVNARALIAESVPNGPSSMTIEACQSVCKGLGYTLA   972
Bgn13.1 -------------------------------------------------------

Cbeg1   -------------------------------------------------------
Exg1    -------------------------------------------------------
ExgA    -------------------------------------------------------
Trexo   GLEYADECYCGNSLANGATIAPDGNAGCNMNCAGNAAETCGGPNRLDIYSYGQANGTQPL   1032
Bgn13.1 -------------------------------------------------------
```

FIG. 2D

```
Cbeg1    GNFVSARTSGAKGDGSTDDTTALQNAINSVASSG-KILFLDHG-HYKITKT------
Phi-29   ----SVKTYGAKGDGVTDDIRAFEKAIESGFPVY-----VPYG-TFMVSRG------
AlgE7    --------GAKGDGKTDDTDAIQAAIDAAHKAGGGTVYLPSG-EYRVSGGDEASDGALI
Endo-N   ----ARGWGAKGDGVTDDTAALTSALNDTPVGQKIN--G-NGKTYKVTSLP---DISRF
Exopg    GAAVDVKASGAKGDGKTDDSAAFAAAWKEACAAG-STITVPKG-EYMVES------LE Cbeg1    LYLPP-----
Phi-29   IKLP------
AlgE7    IKSNVYIVGA
Endo-N   INTRF-----
Exopg    FKGP------
```

FIG. 3

```
N-terminal  --MRLLSFFSCLLAAGGP--------ASALALPSPIANDATSAPLEERQASSYWLENIQH          50
C-terminal  LILENIALNNVPVAVKGPSGTVLAGGTTTIAGWGQGNQYTPGGPTKFQGAITPVRPAGLL         397

N-terminal  QGRAAFN-ANP-----AGYKVFRNVKDYGAKGDGVTDDSAAINAAIADGNR--CAPWVCDS         103
C-terminal  DGKNFYAKSKPQYETVAVGNFVSARTSGAKGDGSTDDTTALQNAINSVASSGKILFLDHG         457

N-terminal  STDTPAIVYFPSGTYVIGK--PIIMYYMTQLHGNPNNRPVLKASPN-------LRAIALI         154
C-terminal  HYKITKTLYLPPGTKIVGETYPIILASGSTWNSKTNPVPVVQVGKAGESGSVELSDFLIG         517

N-terminal  DASP-------YQDGTGKPG--WTS-TNVFTRQIRNFVIDLTPIPAT-SGAQGIHWPAS         202
C-terminal  TQGPTPGAKLIEYNMATTKGSGMWDVHTRIGGAKGTNLQVAQCPVGSVNDACMAAHTNVH         577

N-terminal  QATSIQDVKIQMNVAANSVH--------VGIFIENGSGGHLTDIETVGG-----LHGL         247
C-terminal  ITKSANNVYMENNWFWTADHDLDDSVSTQISIFVGRGLLVEGTNIWLYGNGAEHQSLYQY         637

N-terminal  NVGNQQ---------FTMKNIVISNAVVGINQIWN-------------------         273
C-terminal  QFANAKDVFAGFIQSETPYYMPTPDAKSQPYPVNSALNDPDYNTICPSGQRCDALGLRVL         697

N-terminal  -------WGWLWKGLTISDCSTAAFSMKSLKDNS------PDQNVASVIIDSTITNCPI         320
C-terminal  NSSNVLLYGEGFYSFFISNNNSCSKNTNSVRDCQNRMVSIEGSSTVRAYSLNEVGALQML         757

N-terminal  FVD-----SAWTRTSTAAGSGQ--------         337
C-terminal  TVDGVDKADWMPNLSGYANTIGYFSYNI                                         785
```

FIG. 4

CONIOTHYRIUM MINITANS β-(1,3) EXOGLUCANASE GENE CBEG 1

CROSS-REFERENCE TO RELATED APPLICATIONS

This application claims the benefit of U.S. Provisional Patent Application Serial No. 60/170,168, filed on Dec. 10, 1999. To the extent that it is consistent herewith, the aforementioned application is incorporated herein by reference in its entirety.

FIELD OF THE INVENTION

The invention pertains to a β-(1,3) exoglucanase gene of *Coniothyrium minitans*.

BACKGROUND OF THE INVENTION

The plant cell wall provides stability, protects against pathogens, and influences the growth and development of the plant cell, among other functions. Structurally, the plant cell wall consists of a primary and a secondary wall, both containing cellulose microfibrils embedded in a matrix of carbohydrates (specifically polysaccharides), structural glycoproteins, enzymes, and other components. Carbohydrate polymers have been well characterized and play a primary role in maintaining the structural rigidity of the plant cell wall. In this regard, the plant cell wall sequesters significant amounts of metabolically inactive polysaccharides from among the following classes:

i) celluloses (insoluble fibrils of β-(1,4) glucans);
ii) hemi-celluloses (non-cellulosic polysaccharides which include β-(1,3) glucans, β-(1,3))(1,4) glucans, mannans, and xylans); and
iii) lignin (a polyphenolic compound) (Thomson, 1993).

The β-glucans are polymers of glucose molecules formed by β-links between the glucose molecules. The links may be β-(1,4), β-(1,3), or β-(1,6) or a mixture of those in such polymers. β-glucans are ubiquitous in the natural flora. Many classes of β-glucan polymers exist, and their chemical structure, physiological function, and predominance differ among plant and fungal species.

A. Cellulosic β-Glucans

Cellulosic β-(1,4) glucans are polymeric chains formed by successive glucose monomers covalently joined by β-(1,4) glucan linkages. These β-(1,4) glucan chains associate In bundles to form rigid, insoluble microfibrils which may contain up to several hundred cellulosic polymers (Beguin and Aubert, 1994). The tensile strength of such cellulose microfibrils in the plant cell wall selves to confer rigidity to plant structures. Further, cellulosic components, together with other polymeric compounds in the plant cell wall, demonstrate a protective role by acting as a barrier to various phytopathogens.

B. Non-cellulosic β-Glucans

While cellulosic polymers are ubiquitous in the cell walls of diverse plant species, non-cellulosic glucans (β-(1,3) glucans and β-(1,3)(1,4) glucans) are typically present in the cell walls of some monocotyledonous plant families, such as the Poaceae (Gramineae) (Chesson et al., 1995). In fungi, non-cellulosic β-(1,3) glucans are predominant in the cell wall, notably providing structural resilience (Borgia and Dodge, 1992). In addition to providing structural stability to the fungal cell wall, β-(1,3) glucans serve as carbohydrate reserves in nutritionally-depleted growth environments (Copa-Patino et al., 1989).

The hydrolysis of non-cellulosic β-glucans by β-glucanase enzymes is of great significance to plant-mycopathogen interactions, fungal cell wall architecture, and forage feed digestion in ruminants (Umemoto et al., 1997; Vasquez-Garciduenas et al., 1998; Chen et al., 1997). Such enzymes have been classified into different families according to their origin (plant, fungal, or microbial), substrate specificity, and function (Table 1). Different non-cellulosic β-glucanases thus have distinct substrates and modes of hydrolytic action, to the extent that plant, fungal, and microbial non-cellulosic β-glucanases each belong to specific families with conserved sequence and functional properties.

i) Non-Cellulosic β-Glucanases in Plants

In plants, non-cellulosic glucanases may be classified as either β-(1,3) endoglucanases (laminarinases) or β-(1,3)(1,4) glucanases (mixed linkage glucanases or lichenases) according to substrate specificity and function (Table 1). β-(1,3) endoglucanases (EC 3.2.1.39) hydrolyze successive β-(1,3) glucan (laminarin) chains in an endoglucanase manner (i.e. random digestion within the polymeric chain), whereas β-(1,3)(1,4) glucanases (EC 3.2.1.73) specifically degrade mixed-linkage glucans (non-cellulosic glucans containing glycosidic β-(1,3) and β-(1,4) linkages such as lichenan) by hydrolyzing a β-(1,4) linkage adjacent to a β-(1,3) linkage in the same manner (Hoj and Fincher, 1995).

In addition to targeting different substrates, β-(1,3) endoglucanases and β-(1,3)(1,4) glucanases are distinct functionally. β-(1,3) endoglucanases appear to comprise a large family of pathogenesis-related proteins produced by plants during infection by pathogens. During the plant-pathogen interaction between soybean plants (Glycine max) and the fungal pathogen *Phytophthora megaspora* f. sp. glycinea, soybean β-(1,3) endoglucanases are able to digest the fungal cell walls (Umemoto et al., 1997). The liberated fungal β-(1,3) oligoglucans subsequently bind a β-oligoglucan receptor in the plant cell membrane, initiating a signal transduction event, and ultimately stimulating plant defense responses such as phytoalexin accumulation. β-(1,3) endoglucanases thus appear to weaken and degrade fungal cell walls, while liberating elicitor compounds (such as β-oligoglucan) in order to upregulate plant defense responses.

In comparison, β-(1,3)(1,4) glucanases may play an important role in nutrient mobilization during seed germination in some plant species. During barley (*Hordeum vulgare*) seed germination, the β-(1,3)(1,4) glucanases degrade the β-(1,3)(1,4) glucan-rich cell wall in the seed endosperm, allowing the diffusion of amylases and proteases into starch and protein stores in the endosperm compartment (Hoj and Fincher, 1995).

Although β-(1,3) endoglucanases thus differ functionally from β-(1,3)(1,4) glucanases, these glucanase types in plants are structurally conserved, appearing to originate from a common ancestor (Hoj and Fincher, 1995).

ii) Non-Cellulosic β-Glucanases in Fungi

In comparison to β-(1,3) endoglucanases and β-(1,3)(1,4) glucanases in plants, fungal glucanases differ in both sequence and function (Table 1). In fungi, non-cellulosic glucanases consist of the following classes: β-(1,3) exoglucanase (EC 3.2.1.58); β-(1,3) endoglucanase (EC 3.2.1.39); β-(1,3)(1,4) endoglucanase (EC 3.2.1.73); and β-(1,3)/(1,3) (1,4) glucanase (EC 3.2.1.6). Fungal β-(1,3) exoglucanases are quintessential enzymes in mycoparasitism. Mycoparasites, such as *Trichoderma hazarium*, rely on β-(1,3) exoglucanases to hydrolyze the cell wall of various fungal phytopathogens, thus liberating nutritionally available oligoglucans for absorption and metabolism (Vasquez-Garciduenas et al., 1998). Further, fungal β-(1,3) exoglucanases have been implicated in the autolysis of fungal cell walls in nutritionally-depleted environments (Copa-Patino et al., 1989; Stahmann et al., 1993). In addition, β-(1,3) exoglucanases may have a morphogenic role in fungal growth and differentiation (Peberdy, 1990).

The prevalence of β-(1,3)(1,4) endoglucanases in fungi has yet to be confirmed. To date, few of these have been cloned, with the pioneering example being a mixed-linkage glucanase from the ruminal anaerobic fungus Orpinomyces (licA) (Chen et al., 1997). Such mixed-linkage glucanases from ruminal organisms are presumably produced to improve the digestibility of non-cellulosic β-glucans from fibrous forage feed.

iii) Non-Cellulosic β-Glucanases in Bacteria

In bacteria, non-cellulosic glucanases consist of β-(1,3)(1,4) glucanases (EC 3.2.1.73), which are specific for the substrate, β-(1,3)(1,4) glucan (Table 1). Examples of such microbial glucanases include enzymes from ruminal and non-ruminal microbial species (e.g. *Fibrobacter succinogenes* and *Bacillus subtilis* respectively) (Teather and Erfle, 1990; Wolf et al., 1995).

iv) Non-Cellulosic β-Glucanases in Lower Animalia

A metazoan β-(1,3) endoglucanase from the sea urchin *Strongylocentrotus purpuratus* has been characterized, apparently having a bacterial origin (Bachman and McClay, 1996). Its presence in sea urchin eggs implies that the enzyme may have a glucanolytic function in embryogenesis. Although the role of β-glucanases in metazoans remains obscure, the mere presence of β-glucanases in natural flora and fauna demonstrates the significance of glucanohydrolytic enzymes among a diverse spectrum of biological systems.

v) Applications for Non-Cellulosic β-Glucanases

The developing interest in non-cellulosic β-glucanases ranges from the elucidation of their basic enzymatic action to their numerous industrial applications. Although they have yet to be used extensively in commercial applications, non-cellulosic β-glucanases have already been used to hydrolyze and clarify barley β-glucan in brewing processes (Bamforth, 1980).

Specific interest in non-cellulosic β-glucanases has stemmed from the production of plant β-(1,3) endoglucanases in response to fungal infection. Although such enzymes participate in pathogen responses with some degree of efficacy, the incorporation of a β-(1,3) glucanase with superior hydrolytic activity into a pathogen response regimen may improve plant resistance to fungi. In this regard, compatible β-(1,3) glucanase genes may be incorporated into a transgenic plant line under the transcriptional regulation of a pathogen-responsive promoter.

Furthermore, the development of non-cellulosic β-(1,3)(1,4) glucanases in ruminant microbial technology may increase the efficiency by which non-cellulosic fiber (such as barley β-glucan) is digested. Hence, compatible glucanolytic genes may be incorporated into ruminant microbial or fungal species to improve fiber digestion and nutritive carbohydrate availability from forage feed. Acquisition and characterization of novel non-cellulosic β-glucanases are thus essential towards the use of glucanase genes in various transgenic applications, and the study of the functional flexibility of β-glucanase enzymes.

*Coniothyrium minitans* is a higher eukaryotic fungal mycoparasite which is ubiquitous in soil and non-pathogenic to plants and animals. *C. minitans* exhibits marked β-glucanolytic properties, indicating potential for its development in biotechnological and transgenic applications. *C. minitans* culture supernatants have been previously shown to be effective in hydrolyzing fungal residue of the phytopathogenic organism *Sclerotinia sclerotiorum* (Lib.) de Bary by cooperative activity of β-(1,3) exo- and β-(1,3) endoglucanases (Jones et al., 1974). Additionally, the production of extracellular β-glucanohydrolases was induced by the presence of β-glucan-rich complex carbohydrate sources found in fungal cell walls (International Publication No. WO 99/02662 to Huang et al.). *C. minitans* β-glucanases have also been implicated in *S. sclerotiorum* hyphal and sclerotial invasion, penetration, and degradation (Huang and Hoes, 1976; Huang and Kokko, 1987; Huang and Kokko, 1988).

Fungal non-cellulosic β-glucanases are rare enzymes for which only a few sequences are presently known and available for comparison and functional extrapolation to their homologous counterparts. Isolation and characterization of novel fungal β-glucanases will consolidate functional studies based on gene sequence homologies. Moreover, the discovery of novel glucanolytic sequences will actively contribute to an expanding database containing potential sequences for various biotechnological applications.

TABLE I

Survey of non-cellulosic glucanases: origin, substrate specificities, and function

| Organism | Enzyme | Enzyme classification EC number | Family* | Substrate specificity | Function(s) |
| --- | --- | --- | --- | --- | --- |
| Lower Animalia | β-(1,3) endoglucanase | EC 3.2.1.39 | N/A** | β-(1,3) glucan | Only example is found in sea urchin, may have a role in embryogenesis. |
| Plant | β-(1,3) endoglucanase | EC 3.2.1.39 | 17 | β-(1,3) glucan (laminarin) | Elicitor signal transduction. Part of pathogenesis-related protein (fungal cell wall degradation). |
| Fungi | β-(1,3)(1,4) glucanase | EC 3.2.1.73 | N/A** | β-(1,3)(1,4) glucan (lichenan) | Germination of barley seeds. |
| | β-(1,3) exoglucanase | EC 3.2.1.58 | 5, some in a novel class | β-(1,3) glucan | Mycopathogenesis, autolysis during nutritional stress, cell wall restructuring processes. |
| | β3-(1,3) endoglucanase | EC 3.2.1.39 | N/A** | β-(1,3) glucan | Examples of these have yet to be cloned. Role of β-(1,3) endoglucanases are suspected to be similar to fungal β-(1,3) exoglucanases. |
| | β-(1,3)(1,4) endoglucanase | EC 3.2.1.73 | N/A** | β-(1,3)(1,4) glucan | Orpinomyces licA lichenase; digestion of forage fiber. |

TABLE I-continued

Survey of non-cellulosic glucanases: origin, substrate specificities, and function

| Organism | Enzyme | Enzyme classification EC number | Family* | Substrate specificity | Function(s) |
| --- | --- | --- | --- | --- | --- |
| | β-(1,3)/(1,3)(1,4) glucanase | EC 3.2.1.6 | N/A** | β-(1,3) glucan and β-(1,3)(1,4) glucan | From *Rhizopus arrhizus*, function unclear. |
| Bacteria | β-(1,3)(1,4) glucanase | EC 3.2.1.73 | 16 | β-(1,3)(1,4) glucan | Forage fiber digestion in ruminant bacteria. Also found in non-ruminant bacteria (*Bacillus lichenformis*) presumably functions in metabolic catalysis. |

*Enzyme family classification according to Henrissat and Bairoch, 1993 and Henrissat et al., 1989.
**Enzymes belonging to a novel enzyme family, not classified by existing classification schemes.

SUMMARY OF THE INVENTION

The invention provides a novel β-(1,3) exoglucanase gene (denoted herein as cbeg1) of the soil-borne fungus Coniothyrium minitans. The DNA sequence of the cbeg1 gene and the deduced amino sequence of the encoded β-(1,3) exoglucanase Cbeg1 are depicted in SEQ ID NOS: 1 and 2 respectively. The invention extends to polypeptides possessing β-(1,3) exoglucanase activity, and which comprise amino acid sequences having a length of at least 50 amino acid residues, more preferably at least 100 amino acid residues, more preferably at least 200 amino acid residues, more preferably at least 500 amino acid residues, more preferably at least 600 amino acid residues, more preferably at least 700 amino acid residues, and most preferably at least 750 amino acid residues to the amino acid sequence depicted in SEQ ID NO: 2. In addition, the invention extends to polypeptides possessing β-(1,3) exoglucanase activity, and which comprise amino acid sequences having at least 70%, more preferably at least 75%, more preferably at least 80%, more preferably at least 85%, more preferably at least 90%, and most preferably at least 95% homology to the amino acid sequence depicted in SEQ ID NO: 2.

The cbeg1 gene is compatible with a eukaryotic heterologous expression system, making it particularly useful for a wide range of industrial applications, such as improvement of plant resistance to fungal phytopathogens or use in non-ruminant and ruminant microbial transgenic strategies to improve feed digestion and nutritive carbohydrate availability from forage feed, whereby Cbeg1 degrades the cell wall from plants, particularly within the Poaceae.

In addition, the high activity of Cbeg1 over broad pH and temperature ranges provides benefits in high temperature industrial applications, such as bleaching of pulp, which require temperatures greater than 37° C. Further, Cbeg1 complements degradation initiated by endoglucanases which release oligoglucans, in that β-(1,3) exoglucanase sequentially hydrolyzes β-(1,3) glucan fragments and is required to hydrolyze oligoglucan fragments completely to obtain D-glucose, which can be assimilated. Further, Cbeg1 benefits the plant itself by degrading the cell walls of pathogenic fungi without affecting plant cell walls in dicots, and controlling and stimulating expansion of the cell wall to promote plant growth in monocots and dicots.

Encoded β-(1,3) exoglucanase Cbeg1 is specific for the substrate laminarin, a β-(1,3) glucan with some β-(1,6) linkages, which serves as a carbon reserve polysaccharide in Laminaria and other brown algae (Phaeophyta). Further, Cbeg1 is specific for only laminarin, in that results showed no activity with other substrates tested, such as carboxymethylcellulose, barley β-glucan, lichenan, oat spelt xylan and birchwood xylan. The pH and temperature optima for β-(1,3) exoglucanase Cbeg1 are 6.0 and 57° C., respectively. Cbeg1 contains 784 amino acids, and has a predicted isoelectric point (pI) of 6.0 and molecular weight of 83,646 Daltons.

The invention further provides vectors and cells comprising a nucleic acid molecule encoding the cbeg1 gene, and methods for producing β-(1,3) exoglucanase Cbeg1.

As used herein and in the claims, the terms and phrases set out below have the following definitions.

A "β-(1,3) exoglucanase" is an enzyme that catalyzes the successive hydrolysis of beta-D-glucose units from the non-reducing ends of 1,3-beta-D-glucans, releasing alpha-glucose. The Official Name for β-(1,3) exoglucanase, as recommended by the International Union of Biochemistry and Molecular Biology ("IUBMB") is "glucan 1,3-beta-glucosidase", and its Enzyme Commission ("EC") number is (EC 3.2.1.58). Similarly, a "polypeptide having β-(1,3) exoglucanase activity" is a polypeptide that catalyzes the successive hydrolysis of beta-D-glucose units from the non-reducing ends of 1,3-beta-D-glucans, releasing alpha-glucose.

A "β-glucan" is a polymer of glucose molecules formed by β-links between the glucose molecules. The links may be β-(1,4), β-(1,3), or β-(1,6) or a mixture of those in such a polymer.

"Coding sequence" means the part of a gene which codes for the amino acid sequence of a protein, or for a functional RNA such as a tRNA or rRNA.

"Complement" or "complementary sequence" means a sequence of nucleotides which forms a hydrogen-bonded duplex with another sequence of nucleotides according to Watson-Crick base-pairing rules. For example, the complementary base sequence for 5'-AAGGCT-3" is 3'-TTCCGA-5'.

A "domain" of a polypeptide is a portion or region of the polypeptide that forms a structural or functional niche within the remainder of the polypeptide. For example, DNA-binding proteins have DNA-binding domains with specific features such as helix-turn-helix configurations or $Zn^{2+}$-fingers which enable them to recognize and bind to specific structures or sequences on their target DNA with high specificity and affinity.

"Downstream" means on the 3' side of any site in DNA or RNA.

"Expression" refers to the transcription of a gene into structural RNA (rRNA, tRNA) or messenger RNA (mRNA) with subsequent translation into a protein.

An amino acid sequence that is "functionally equivalent" to *C. minitans* Cbeg1 is an amino acid sequence that has been modified by single or multiple amino acid substitutions, by addition and/or deletion of amino acids, or where one or more amino acids have been chemically modified, but which nevertheless retains the β-(1,3) exoglucanase activity of *C. minitans* Cbeg1.

"Functionally equivalent" nucleotide sequences are those that encode polypeptides having substantially the same biological activity.

Two nucleic acid sequences are "heterologous" to one another if the sequences are derived from separate organisms, whether or not such organisms are of different species, as long as the sequences do not naturally occur together in the same arrangement in the same organism.

Two polynucleotides or polypeptides are "homologous" or "identical" if the sequence of nucleotides or amino acid residues, respectively, in the two sequences is the same when aligned for maximum correspondence as described herein. Sequence comparisons between two or more polynucleotides or polypeptides are generally performed by comparing portions of the two sequences over a comparison window to identify and compare local regions of sequence similarity. The comparison window is generally from about 20 to about 200 contiguous nucleotides or contiguous amino acid residues. The "percentage of sequence identity" or "percentage of sequence homology" for polynucleotides and polypeptides may be determined by comparing two optimally aligned sequences over a comparison window, wherein the portion of the polynucleotide or polypeptide sequence in the comparison window may include additions or deletions (i.e., gaps) as compared to the reference sequence (which does not comprise additions or deletions) for optimal alignment of the two sequences. The percentage is calculated by: (a) determining the number of positions at which the identical nucleic acid base or amino acid residue occurs in both sequences to yield the number of matched positions; (b) dividing the number of matched positions by the total number of positions in the window of comparison; and, (c) multiplying the result by 100 to yield the percentage of sequence identity.

Optimal alignment of sequences for comparison may be conducted by computerized implementations of known algorithms, or by inspection. A list providing sources of both commercially available and free software is found in Ausubel et al. (2000). Readily available sequence comparison and multiple sequence alignment algorithms are, respectively, the Basic Local Alignment Search Tool (BLAST) (Altschul e al., 1997) and ClustalW programs. Other suitable programs include GAP, BESTFIT, FASTA, and TFASTA in the Wisconsin Genetics Software Package (Genetics Computer Group (GCG), 575 Science Dr., Madison, Wis.). For greater certainty, as used herein and in the claims, "percentage of sequence identity" or "percentage of sequence homology" of amino acid sequences is determined based on optimal sequence alignments determined in accordance with the default values of the BLASTX program, available as described above.

As discussed in greater detail hereinafter, homology between nucleotide sequences can also be determined by DNA hybridization analysis, wherein the stability of the double-stranded DNA hybrid is dependent on the extent of base pairing that occurs. Conditions of high temperature and/or low salt content reduce the stability of the hybrid, and can be varied to prevent annealing of sequences having less than a selected degree of homology.

"Hemicellulose" includes glucans (apart from starch), mannans, xylans, arabinans or polyglucuronic or polygalacturonic acid.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated", but the same polynucleotide or polypeptide separated from the coexisting materials of its natural state is "isolated", as the term is employed herein.

"Laminarin" means a polymer of β-(1,3) glucan with some β-(1,6) linkages, which serves as a carbon reserve polysaccharide in Laminaria and other brown algae (Phaeophyta).

A "polynucleotide" is a linear sequence of deoxyribonucleotides (in DNA) or ribonucleotides (in RNA) in which the 3' carbon of the pentose sugar of one nucleotide is linked to the 5' carbon of the pentose sugar of the adjacent nucleotide via a phosphate group.

A "polynucleotide construct" is a nucleic acid molecule which is isolated from a naturally occurring gene or which has been modified to contain segments of nucleic acid which are combined and juxtaposed in a manner which would not otherwise exist in nature.

Two DNA sequences are "operably linked" if the nature of the linkage does not interfere with the ability of the sequences to effect their normal functions relative to each other. For instance, a promoter region would be operably linked to a coding sequence if the promoter were capable of effecting transcription of that coding sequence.

A "polypeptide" is a linear polymer of amino acids that are linked by peptide bonds.

"Promoter" means a cis-acting DNA sequence, generally 80–120 base pairs long and located upstream of the initiation site of a gene, to which RNA polymerase may bind and initiate correct transcription.

A "recombinant" nucleic acid molecule, for instance a recombinant DNA molecule, is a novel nucleic acid sequence formed in vitro through the ligation of two or more nonhomologous DNA molecules (for example a recombinant plasmid containing one or more inserts of foreign DNA cloned into its cloning site or its polylinker).

"Transformation" means the directed modification of the genome of a cell by the external application of purified recombinant DNA from another cell of different genotype, leading to its uptake and integration into the subject cell's genome. In bacteria, the recombinant DNA is not integrated into the bacterial chromosome, but instead replicates autonomously as a plasmid.

A "transgenic" organism, such as a transgenic plant, is an organism into which foreign DNA has been introduced. A "transgenic plant" encompasses all descendants, hybrids, and crosses thereof, whether reproduced sexually or asexually, and which continue to harbour the foreign DNA.

"Upstream" means on the 5' side of any site in DNA or RNA.

A "vector" is a nucleic acid molecule that is able to replicate autonomously in a host cell and can accept foreign DNA. A vector carries its own origin of replication, one or more unique recognition sites for restriction endonucleases which can be used for the insertion of foreign DNA, and usually selectable markers such as genes coding for antibiotic resistance, and often recognition sequences (e.g. promoter) for the expression of the inserted DNA. Common vectors include plasmid vectors and phage vectors.

BRIEF DESCRIPTION OF THE DRAWINGS

FIGS. 1A and 1B are a sequence alignment of three fungal β-(1,3) exoglucanase genes used in the construction of semi-degenerate β-(1,3) exoglucanase-specific PCR primers (SEQ ID NOS: 3, 7, 8, 12, and 13) used in the examples. The sources of β-(1,3) exoglucanase sequences are:

(1) *Ampelomyces quisqualis* (Rotem et al., 1997; GenBank accession no. AF029354) SEQ ID NOS: 4 and 9;
(2) *Cochliobolus carbonum* (Schaeffer et al., 1994; GenBank accession no. L48994) SEQ ID NOS: 5 and 10;
(3) *Trichoderma harzianum* (Cohen-Kupiec et al., 1999; GenBank accession no. AJ002397) SEQ ID NOS: 6 and 11.

FIGS. 2A, 2B, 2C and 2D are an amino acid sequence comparison of the deduced amino acid sequence (SEQ ID NO: 2) of the Cbeg1 β-(1,3) exoglucanase encoded by the *C. minitans* cbeg1 β-(1,3) exoglucanase gene, with representative fungal β-(1,3) exoglucanases and a β-(1,3)(1,4) endoglucanase. Sequences were aligned using the CLUSTALW alignment algorithm. The glucanases depicted are as follows:

(1) Cbeg1, *Coniothyrium minitans* (fungal mycoparasite) SEQ ID NO: 2;
(2) Exg1, *Cochliobolus carbonum* (fungus, Schaeffer et al., 1994; GenBank accession no. L48994) SEQ ID NO: 14;
(3) ExgA, *Ampelomyces quisqualis* (fungus, Rotem et al., 1997; GenBank accession no. AF029354) SEQ ID NO: 15;
(4) Trexo, *Trichoderma harzianum* β-(1,3) exoglucanase (fungal mycoparasite, Cohen-Kupiec et al., 1999; GenBank accession no. AJ002397) SEQ ID NO: 16; and
(5) Bgn13.1, *Trichoderma harzianum* β-(1,3)(1,4) endoglucanase (fungal mycoparasite, de la Cruz et al., 1995; GenBank accession no. X84085) SEQ ID NO: 17.

Conserved amino acid residues are highlighted in bold. GAK (amino acids 63 to 82) and GAX (amino acids 425 to 435) boxes are underlined.

FIG. 3 is a GAX box alignment among a portion of the deduced amino acid sequence of the Cbeg1 β-(1,3) exoglucanase encoded by the *C. minitans* cbeg1 β-(1,3) exoglucanase gene (amino acids 416 to 464 of SEQ ID NO: 2) and partial sequences of non-glucanolytic enzymes aligned using the CLUSTALW alignment algorithm. Conserved amino-acid residues are highlighted in bold. The non-glucanolytic enzymes depicted are as follows:

(1) Phi-29, a neck appendage protein from a Bacillus bacteriophage phi-29 (Vlcek and Paces, 1986; GenBank accession no. M14782) SEQ ID NO: 18;
(2) AlgE7, a mannuronan C5 epimerase from the bacterial species *Azotobacter vinelandii* (Svanem et al., 1999; GenBank accession no. AF099800) SEQ ID NO: 19;
(3) Endo-N, endo-N-acylneuraminidase from a bacteriophage K1F (Petter and Vimr, 1993; GenBank accession no. M63657) SEQ ID NO: 20; and
(4) Exopg, an exopolygalacturonase from *Arabidopsis thaliana* (Torki et al., 1999; GenBank accession no. X72292) SEQ ID NO: 21.

FIG. 4 is a comparison of the GAK (N-terminal) and GAX (C-terminal) boxes of the deduced amino acid sequence of the Cbeg1 β-(1,3) exoglucanase encoded by the *C. minitans* cbeg1 β-(1,3) exoglucanase gene. Sequences were aligned with the CLUSTALW alignment algorithm. Conserved amino-acid residues are highlighted in bold. The N-terminal region of the sequence includes amino acids 1 to 337 of SEQ ID NO: 2 and the C-terminal region includes amino acids 338 to 785 of SEQ ID NO: 2.

DETAILED DESCRIPTION OF THE PREFERRED EMBODIMENTS

The invention provides a novel β-(1,3) exoglucanase gene obtained from Coniothyrium minitans, and denoted cbeg1. The nucleotide sequence of the cbeg1 gene is set forth in SEQ ID NO: 1. The open reading frame is indicated by the corresponding amino acids underneath (extending from nucleotide 25 to nucleotide 2379). The putative signal peptide extends from amino acid 1 to 21. The cbeg1 gene encodes a polypeptide having β-(1,3) exoglucanase activity, and denoted *C. minitans* glucanase Cbeg1. The deduced amino acid sequence of the encoded Cbeg1 β-(1,3) exoglucanase is depicted in SEQ ID NO: 2.

It will be appreciated by those of skill in the art that, due to the degeneracy of the genetic code, numerous functionally equivalent nucleotide sequences encode the same amino acid sequence. All nucleotide sequences that encode the Cbeg1 β-(1,3) exoglucanase sequence depicted in SEQ ID NO: 2 are included in the invention.

Further, strains of *C. minitans* may contain naturally occurring allelic variants of the cbeg1 gene which encode variants of Cbeg1 having β-(1,3) exoglucanase activity that is substantially the same as that of the Cbeg1 sequence depicted in SEQ ID NO: 2. All such allelic variants of the cbeg1 gene and the encoded Cbeg1 β-(1,3) exoglucanase are included within the scope of the invention.

Using the techniques described in detail in the Examples herein, the cbeg1 gene sequence depicted in SEQ ID NO: 1 or the encoded Cbeg1 protein sequence depicted in SEQ ID NO: 2 can be used to design primers (such as the Gf1/Gr1 primer pair described in the Examples herein) for amplification of homologous sequences in *C. minitans* or other organisms by polymerase chain reaction (PCR), or for the construction of labeled probes (e.g. biotin-labeled, radio-labeled) for use in nucleic acid hybridization assays to identify homologous nucleic acid sequences. Such sequences can then be tested by the methods described in the Examples herein for the expression of polypeptides having β-(1,3) exoglucanase activity. By these methods, those skilled in the art can identify different alleles of the cbeg1 β-(1,3) exoglucanase gene, or variant nucleotide sequences that encode polypeptides having β-(1,3) exoglucanase activity.

Additionally, those skilled in the art can obtain altered cbeg1 gene sequences and test them for the expression of polypeptides having β-(1,3) exoglucanase activity through standard mutagenesis techniques in conjunction with the β-(1,3) exoglucanase activity assays described in the Examples herein. Useful mutagenesis techniques known in the art include, without limitation, oligonucleotide-directed mutagenesis, region-specific mutagenesis, linker-scanning mutagenesis, and site-directed mutagenesis by PCR (Sambrook et al., 1989: Ausubel et al., 2000). A method of generating variants of the nucleotide sequences can also be obtained by changing nucleotides through addition or deletion of nucleotides within the sequence and testing the encoded polypeptide for activity (International Publication No. WO 00/18909 to Swanson et al.).

In obtaining variant cbeg1 coding sequences, those skilled in the art will recognize that proteins may be modified by certain amino acid substitutions, additions, deletions, and post-translational modifications, without loss or reduction of biological activity. In particular, it is well-known that conservative amino acid substitutions, that is, substitution of one amino acid for another amino acid of similar size, charge, polarity and conformation, are unlikely to significantly alter protein function. The 20 standard amino acids that are the constituents of proteins can be broadly categorized into four groups of conservative amino acids as follows: the nonpolar (hydrophobic) group includes alanine, isoleucine, leucine, methionine, phenylalanine, proline, tryptophan and valine; the polar (uncharged, neutral) group includes asparagine, cysteine, glutamine, glycine, serine, threonine and tyrosine; the positively charged (basic) group contains arginine, histidine and lysine; and the negatively charged (acidic) group contains aspartic acid and glutamic acid. Substitution in a protein of one amino acid for another within the same group is unlikely to have an adverse effect on the biological activity of the protein.

As shown in FIGS. 2A–2D, Cbeg1 β-(1,3) exoglucanase exhibits homology to other fungal β-(1,3) exoglucanases and a β-(1,3)(1,4) endoglucanase. Among the glucanases compared, Cbeg1 exhibits the greatest homology to Exg1, *Cochliobolus carbonum* (Schaeffer et al., 1994) with an overall homology of 59% over the whole sequence. The homologies of Cbeg1 are 51% with Trexo, *Trichoderma harzianum* β-(1,3) exoglucanase (Cohen-Kupiec et al., 1999); 43% with ExgA, *Ampelomyces quisqualis* (Rotem et al., 1997); and 26% with Bgn13. 1, *Trichoderma harzianum* β-(1,3)(1,4) endoglucanase (de la Cruz et al., 1995). Homologies of Cbeg1 with recently discovered GLUC78, *Trichoderma atroviride* glucan 1,3-β-glucosidase (Donzelli et al., 2000) and Cmg1, *Coniothyrium minitans* β-(1,3) glucanase (Giezey et al., 2000) were 44% and 42% respectively It is well-known in the art that individual amino acids or sequences of amino acids that are essential to the biological activity of a protein are closely conserved among related proteins, in accordance with principles of natural selection. Thus, those of skill in the art will recognize that substitutions, additions, deletions, and modifications of amino acids within the Cbeg1 sequence at non-conserved regions will be less likely to negatively affect the glucanolytic function of the enzyme than would equivalent changes within highly conserved regions. As such, it is expected that substitutions, additions, deletions, and modifications would be least likely to negatively affect the glucanolytic activity of Cbeg1 if they were to occur in a subregion where there is little or no conservation of the amino acid sequence.

Homology between nucleotide sequences can be determined by DNA hybridization analysis, wherein the stability of the double-stranded DNA hybrid is dependent on the extent of base pairing that occurs. Conditions of high temperature and/or low salt content reduce the stability of the hybrid, and can be varied to prevent annealing of sequences having less than a selected degree of homology. Under the following conditions, the temperature and salt concentration of hybridization and washing conditions can be adjusted to target any specific homology levels. Obtaining a homology of 70% using the coding sequence of cbeg1 (52% GC content) involves hybridizing with 6×SSC (sodium chloride/sodium citrate buffer) and 0.1% SDS (sodium dodecyl sulfate) at 52° C. and washing with 1×SSC and 0.1% SDS at 39° C. By increasing the hybridization and washing temperature in 5° C. increments, the level of homology would increase by 5%. For hybridization and washing temperatures of 57 and 44° C., 62 and 49° C., 67 and 54° C., 68 and 59° C., 68 and 64° C., and 68 and 69° C., the theoretical homology of sequences hybridized with the coding region of cbeg1 would be 75, 80, 85, 90, 95, and 100% respectively.

A wide range of computer programs for comparing nucleotide and amino acid sequences (and measuring the degree of homology) are also available, and a list providing sources of both commercially available and free software is found in Ausubel et al. (2000). Readily available sequence comparison and multiple sequence alignment algorithms are, respectively, the Basic Local Alignment Search Tool (BLAST) (Altschul et al., 1997) and ClustalW programs.

An additional method for comparing nucleotide sequences involves storing a sequence of interest on computer media and using a computer program to compare the stored sequence with reference sequences (International Publication No. WO 00/18909 to Swanson et al.).

In view of the foregoing, nucleotide sequences having at least 70% homology, more preferably at least 75% homology, more preferably at least 80% homology, more preferably at least 85% homology, even more preferably at least 90% homology, and most preferably at least 95% homology with the cbeg1 gene sequence depicted in SEQ ID NO: 1, and which encode polypeptides having glucanolytic activity are within the scope of this invention, as are amino acid sequences having at least 70% homology, more preferably at least 75% homology, more preferably at least 80% homology, more preferably at least 85% homology, even more preferably at least 90% homology, and most preferably at least 95% homology with the Cbeg1 glucanase sequence depicted in SEQ ID NO: 2 and which possess glucanolytic activity. These homology values are based on comparison between the whole length of both sequences encoding a polypeptide at the amino acid or DNA level. Further, these homology values are based on the comparisons of Cbeg1 with other glucanases, with the greatest or closest homology to Exg1, *Cochliobolus carbonum* (Schaeffer et al, 1994) being 59% over the whole sequence.

Thus, in a first embodiment, the invention provides an isolated nucleic acid molecule encoding a polypeptide having glucanolytic activity, the encoded polypeptide comprising the amino acid sequence depicted in SEQ ID NO, 2 from amino acid 1 to amino acid 785, or a functionally equivalent sequence having at least 70% homology, more preferably at least 75% homology, more preferably at least 80% homology, more preferably at least 85% homology, even more preferably at least 90% homology, and most preferably al least 95% homology thereto.

As detailed in Example 4 herein, analysis of the Cbeg1 glucanase sequence depicted in SEQ ID NO: 2 indicates that Cbeg1 has a similar structure as other fungal β(1,3) exoglucanases from *C. carbonum, A. quisqualis*, and *T. harzianum*, since Cbeg1 includes a GAK box extending from amino acids 63 to 82 of SEQ ID NO: 2 and a signal peptide at the N-terminal end (amino acids 1 to 21). It is speculated that this predicted signal peptide could likely be deleted without affecting enzymatic activity. Therefore, in another embodiment, the invention provides an isolated nucleic acid molecule encoding a polypeptide having glucanolytic activity, with the encoded polypeptide comprising the amino acid sequence depicted in SEQ ID NO: 2 from amino acid 22 to 785, or a functionally equivalent sequence having at least 70% homology, more preferably at least 75% homology, more preferably at least 80% homology, more preferably at least 85% homology, even more preferably at least 90% homology, and most preferably at least 95% homology thereto.

Furthermore, Cbeg1 also includes a GAX box spanning amino acids 425 to 434 of SEQ ID NO: 2, which exhibits identity to GAX box regions in genes, such as Phi-29, AlgE7, Endo-N, and Exopg, which have diverse origins and encode non-glucanolytic enzymes with dissimilar functions. In addition, a sequence comparison of the GAK (N-terminal) and GAX (C-terminal) boxes of Cbeg1 indicates conservation of key residues outside a homologous "GDGXTDD" domain (SEQ ID NO: 22). Conservation of this "GDGXTDD" sequence within Cbeg1 and other homologous sequences of disparate origin and function denotes the significance of this domain in glucanolytic function in addition to non-glucanolytic functions evolved in genes derived from this fungal glycosyl hydrolase family.

Cbeg1 is specific for the substrate laminarin, in that results showed no activity with other substrates tested, such as carboxymethylcellulose, barley β-glucan, lichenan, oat spelt xylan and birchwood xylan. The specificity of Cbeg1 for only one substrate is beneficial in that degradation of the exact desired substrate, laminarin, is guaranteed to proceed efficiently. In the event where an enzyme has activity upon more than one substrate, there is no guarantee that degradation of any desired substrate will occur since the enzyme then has unlimited substrates available.

Exo- and endo-glucanases are known to work cooperatively to degrade glucans efficiently (Jones et al., 1974). Cbeg1 may complement degradation initiated by endoglucanases which release oligoglucans, in that β-(1,3) exoglucanase sequentially hydrolyzes β-(1,3) glucan fragments and is required to hydrolyze oligoglucan fragments completely to obtain D-glucose, which can be assimilated.

The pH and temperature optima for Cbeg1 are 6.0 and 57° C., respectively. Cbeg1 displays high activity not only over a broad and high temperature range, with over 80% of activity recorded between 42 and 63° C., but also over a broad pH range, with more than 80% of activity observed between a pH of 4.8 and 6.8. High activity of Cbeg1 over broad pH and temperature ranges is advantageous by ensuring efficient degradation of β-(1,3) glucan. Moreover, since the enzyme is stable at high temperatures and works successfully across such broad ranges, Cbeg1 may be beneficial for use in high temperature industrial applications, such as bleaching of pulp, which require temperatures greater than 37° C.

C. minitans is a higher eukaryotic fungus, belonging to either the Ascomycota or Basidiomycota subphyla, depending on its reproductive regimen. Since the GC content and codon usage are close to those of higher plants, genes isolated from C. minitans are likely to be compatible with other higher eukaryotic systems and may thus be expressed efficiently in both prokaryotic and eukaryotic systems.

In prokaryotes, functional compatibility of Cbeg1 with microbial systems may be of great importance to ruminal biotechnology. The transfer of the Cbeg1 cDNA into ruminal microbial or fungal species, and the overexpression of Cbeg1 in the rumen can increase digestive efficiency of non-N4 cellulosic fiber such as barley β-glucan. Therefore, in further embodiments, the invention extends to cells other than C. minitans transformed with a nucleic acid molecule encoding C. minitans glucanase Cbeg1 or a variant thereof having glucanolytic activity and to methods for producing a polypeptide having glucanolytic activity, comprising culturing such cells under conditions conducive to the expression of the encoded polypeptide and recovering the encoded polypeptide from the culture. The invention also extends to vectors containing nucleic acid molecules of the invention encoding polypeptides having glucanolytic activity. Such vectors will usually also contain at least a promoter and a transcription termination signal.

In eukaryotes, expression of the isolated C. minitans β-(1,3) exoglucanase gene cbeg1 of the invention is demonstrated in Example 5 herein which describes the expression of cbeg1 in the yeast Pichia pastoris. Large quantities of the Cbeg1 enzyme can be produced by Pichia pastoris using a large-scale fermentor. After growth of the yeast, the medium which contains Cbeg1 is withdrawn from the fermentor and enzymatic activity determined. The medium is then prepared in either solid or liquid form. To provide a solid form, the medium may be lyophilized to facilitate handling and preservation. Alternatively to produce a liquid form, an enzyme stabilizer such as glycerol may be added to the medium and the enzyme dispensed as a liquid. Whether the enzyme-containing medium is prepared in either liquid or solid form, sufficient medium should be added to provide 25000 U of enzyme activity per ton of feed for beef cattle. However, the units of enzyme activity to be added to feed may be multiplied by factors of 2, 5, 10 or 50, depending on the nature of the feed (silage or barley grain) and the animal species.

Further, cbeg1 is useful for effecting the recombinant expression of Cbeg1 in plants, as shown in Examples 6 and 7 which describe cbeg1 expression in monocotyledonous (barley cultivar Golden Promise) and dicotyledonous (*Brassica napus* cultivar Westar) plants respectively. Plant species of interest include, without limitation: canola, mustard, or rapeseed (Brassica spp.); flax (Linum spp.); corn (*Zea mays*); soybean (Glycine and Soja spp.); cotton (Gossypium spp.); mouse ear crest (*Arabidopsis thaliana*); wheat (Triticum spp.); rye (Secale spp.); barley (Hordeum spp.); oats (Avena spp.); rice (Oryza spp.); sorghum (Sorghum spp.); potato (Solanum spp.); tomato (Lycopersicon spp.); tobacco (Nicotiana spp.); and Cucurbita spp. (gourd, squash, pumpkin, watermelon, etc.).

Expression of cbeg1 in barley (Hordeum spp.) provides an economical and direct way to supplement this enzyme to the feed of beef cattle. Cbeg1 may facilitate efficient digestion of oligoglucan degraded by ruminal bacteria, thereby increasing percentages of digestibility and energy uptake. Considering the size of the beef cattle industry in North America and worldwide, a few percent increase has tremendous impact.

For making transgenic plants, an appropriate vector must be prepared initially, with suitable recombinant vectors including an expression cassette designed for initiating transcription of the C. minitans β-(1,3) exoglucanase gene cbeg1 in plants. Additional sequences can be included to allow the vector to be cloned in a bacterial or phage host. The vector will preferably contain a prokaryote origin of replication having a broad host range. A selectable marker may also be included to allow selection of bacterial cells bearing the desired construct; for example, suitable prokaryotic selectable markers include those that confer resistance to antibiotics such as ampicillin. Other DNA sequences encoding additional functions may also be present in the vector; for instance, in the case of Agrobacterium mediated transformation, T-DNA sequences will also be included for subsequent transfer to plant chromosomes.

For expression in plants, the recombinant expression cassette preferably contains, in addition to the desired sequence, a promoter region effective in plants, a transcription initiation site (if the sequence to be transcribed lacks one), and a transcription termination sequence. Unique restriction enzyme sites at the 5' and 3' ends of the cassette are typically included to allow for easy insertion into a pre-existing vector. Sequences controlling eukaryotic gene expression are well known in the art.

Transcription of DNA into mRNA is regulated by a region of DNA referred to as the promoter. The promoter region contains a sequence of bases that signals RNA polymerase to associate with the DNA, and to initiate the transcription of mRNA using one of the DNA strands as a template to make a corresponding complementary strand of RNA. Promoter sequence elements include the TATA box consensus sequence (TATAAT), which is usually 20 to 30 bp upstream of the transcription start site. In most instances the TATA box is required for accurate transcription initiation. The TATA box is the only upstream promoter element that has a relatively fixed location with respect to the start point. Another consensus sequence, the CAAT box, is centered at −75, but can function at distances that vary considerably from the start point and in either orientation. Another common promoter element is the GC box at −90 which contains the consensus sequence GGGCGG. It may occur in multiple copies and in either orientation. Other sequences conferring tissue specificity, response to environmental signals, or maximum efficiency of transcription may also be found in the promoter region. Such sequences are often found within 400 bp of transcription initiation size, but may extend as far as 2000 bp or more. In heterologous promoter/structural gene combinations, the promoter is preferably positioned about the same distance from the heterologous transcription start site as it is from the transcription start site in its natural setting. However, some variation in this distance can be accommodated without loss of promoter function.

The particular promoter used in the expression cassette is not critical to the invention. Any of a number of promoters which direct transcription in plant cells is suitable. The promoter can be either constitutive, inducible, tissue specific, or temporal specific. A number of promoters which are active in plant cells have been described in the literature. These include the nopaline synthase (NOS) and octopine synthase (OCS) promoters (which are carried on tumour-inducing plasmids of *Agrobacterium tumefaciens*), the caulimovirus promoters such as the cauliflower mosaic virus (CaMV) 19S and 35S and the figwort mosaic virus 35S-promoters, the light-inducible promoter from the small subunit of ribulose-1,5-bis-phosphate carboxylase (ssRUBISCO, a very abundant plant polypeptide), and the chlorophyll a/b binding protein gene promoter, a cryptic promoter (tCUP) from tobacco, etc. All of these promoters have been used to create various types of DNA constructs which have been expressed in plants. The CaMV 35S promoter, which is used in Example 7 herein, has been shown to be highly active and constitutively expressed in most tissues (Bevan et al., 1986). Other promoters may be used; for example, those for the genes napin and cruciferin (Breen and Crouch, 1992; Scofield and Crouch, 1987).

In addition to a promoter sequence, the expression cassette should contain a transcription termination region downstream of the structural gene to provide for efficient termination. The termination region may be obtained from either the same gene as the promoter sequence or different genes. In the exemplified cases, the nopaline synthase NOS 3'terminator sequence (Bevan et al. 1983) was used.

Polyadenylation is believed to have an effect on stabilizing mRNAs. Therefore, polyadenylation sequences are also commonly added to the vector construct if the mRNA encoded by the structural gene is to be efficiently translated (Alber and Kawasaki, 1982). Polyadenylation sequences include, but are not limited to the Agrobacterium octopine synthase signal (Gielen et al., 1984) or the nopaline synthase signal (Depicker et al., 1982).

The vector will also typically contain a selectable marker gene by which transformed plant cells can be identified in culture. Typically, the marker gene encodes antibiotic resistance or herbicide resistance. These markers include those that confer resistance to the antibiotics G418, hygromycin, bleomycin, kanamycin, gentamycin, and the bar gene which confers herbicide resistance. In exemplified cases, the marker genes confer resistance to kanamycin, and glufosinate ammonium herbicide (Wan and Lemaux, 1994). Those cells containing the vector will be identified by their ability to grow in a medium containing the particular selective agent.

With the objective of plant transformation with Coniothyrium minitans β-(1,3) exoglucanase gene cbeg1, the polynucleotide would be inserted in the sense orientation into the expression cassette.

Once an appropriate vector has been assembled, a variety of techniques are available for introducing foreign DNA into plant cells. In accordance with the invention, bombardment (Weeks et al., 1993; Wan and Lemaux, 1994; Cho et al., 1998) is a preferred method for introducing cbeg1 into cell explants from monocotyledonous plants (e.g. barley, oat, wheat). Alternatively, Agrobacterium mediated transformation has been reported for barley (Tingay et al., 1997). For introduction of *C. minitans* β-(1,3) exoglucanase gene cbeg1 into cell explants from dicotyledonous plants (e.g. canola), Agrobacterium mediated transformation (Tingay et al., 1997; Trick and Finer, 1997) is preferred. Preferred sources of tissue explants include scutella from immature embryos or other tissue undergoing rapid multiplication and differentiation (e.g. meristems, immature inflorescences, callus, microspores, microspore-derived embryos, cell suspensions, and protoplasts).

Other transformation techniques which are known in the art can also be used to transfer the recombinant DNA. For instance, the vector can be micro-injected directly into plant cells. Alternatively, nucleic acids may be introduced to the plant cell by high velocity ballistic penetration with small particles having the nucleic acid of interest embedded within the matrix or alternatively on the surface of the particles. Fusion of protoplasts with lipid-surfaced bodies such as minicells, cells or lysosomes carrying the DNA of interest can be used. The DNA may also be introduced into plant cells by electroporation, wherein plant protoplasts are electroporated in the presence of plasmids carrying the expression cassette. A review of these techniques is found in Gelvin et al. (1994).

The above-mentioned Agrobacterium mediated transformation technique, which is particularly useful for transformation of dicots such as canola, is a form of vectored transformation that uses *Agrobacterium tumefaciens. A. tumefaciens* is a Gram-negative soil bacteria which causes a neoplastic disease known as crown gall in dicotyledonous plants. Induction of tumours is caused by tumour-inducing plasmids known as Ti plasmids, which direct the synthesis of opines or octopines in the infected plant. The opines or octopines are used as a source of carbon and/or nitrogen by the Agrobacterium.

The bacterium does not enter the plant cell, but transfers only part of the Ti plasmid, a portion called T-DNA. The T-DNA becomes stably integrated into the plant genome, where it expresses the functions needed to synthesize opines and to transform the plant cell. Virulence (Vir) genes on the Ti plasmid, outside of the T-DNA region, are necessary for the transfer of the T-DNA. The vir region, however, is not transferred. In fact, the vir region, although required for T-DNA transfer, need not be physically linked to the T-DNA and may be provided on a separate plasmid.

The tumour-inducing portions of the T-DNA can be interrupted or deleted without loss of the transfer and integration functions, such that normal and healthy transformed plant cells may be produced which have lost all properties of tumour cells, but still harbour and express certain parts of T-DNA, particularly the T-DNA border regions. Therefore, modified Ti plasmids, in which the disease causing genes have been deleted, may be used as vectors for the transfer of gene constructs of the present invention.

Transformation of plants cells with Agrobacterium and regeneration of whole plants typically involves either co-cultivation of Agrobacterium with cultured isolated protoplasts or transformation of intact cells or tissues with Agrobacterium. In an exemplified case, petiole explants from Brassica napus plantlets are transformed with Agrobacterium.

When it is desired to transform monocots such as wheat or barley with *C. minitans* β-(1,3) exoglucanase gene cbeg1, biolistic transformation techniques are preferred. The transformation vector preferably includes a rice actin promoter and the first intron of the actin gene (which controls the expression of the bar gene), followed by the bar gene (which confers resistance to glufosinate ammonium herbicide) and the NOS terminator. A second similar vector is also prepared, in which the *C. minitans* β-(1,3) exoglucanase gene cbeg1 of interest is substituted for the bar gene. Plant tissues are co-transformed by bombardment with gold particles coated with both vectors. Co-transformation enables integration of vectors in different location of the genome which will lead to segregation of the marker gene from the gene of interest in subsequent generations when plants are regenerated.

Embryogenic tissue, such as immature scutella dissected from embryos, is preferred for bombardment (Cho et al., 1998; Wan and Lemaux, 1994). The embryonic tissue preferably is obtained from an easily regenerated plant line or cultivar (e.g. var. Golden Promise in barley). Using a micro-projectile bombardment device, embryogenic tissues are bombarded with gold particles that are coated with the DNA constructs of interest, and plants are then regenerated (Wan and Lemaux, 1994).

After transformation, transformed plant cells or plants carrying the introduced DNA are identified, typically by selection for the marker gene. In exemplified cases, transformed plant cells are selected by growing the cells on growth medium containing kanamycin and glufosinate ammonium. Other selectable markers will be apparent to those of skill in the art. For instance, the presence of opines can be used to identify transformants if the plants are transformed with Agrobacterium.

It will be apparent to those of ordinary skill in the art that alternative methods, reagents, procedures and techniques other than those specifically detailed herein can be employed or readily adapted to practice this invention. The invention is further illustrated in the following non-limiting Examples. All abbreviations used herein are standard abbreviations used in the art. Specific procedures not described in detail in the Examples are well-known in the art.

EXAMPLE 1

Cloning and Characterizing a Genomic Glucanase-Like DNA Fragment From *Coniothyrium minitans* i) Genomic DNA Isolation from *Coniothyrium minitans* Strains M11-3B 2A2 A10-4 and 2134

A *Coniothyrium minitans* strain with superior cellulolytic activity (*C. minitans* strain LRS M11-3B 2A2—Lethbridge Research Centre Collection ("LRCC"), Agriculture and Agri-Food Canada, Lethbridge Research Centre, Lethbridge, Alberta, Canada), was generated from a wild-type *C. minitans* strain (LRCC *C. minitans* strain LRS 2134—deposited under accession No. 74415 with the American Type Culture Collection ("ATCC"), located at 10801 University Boulevard, Manassas, Va., 20110-2209, USA), by UV mutagenesis and subsequent screening for improved glycosyl hydrolase activity (International Publication No. WO 99/02662 to Huang et al.). *C. minitans* strain A10-4 (LRCC *C. minitans* strain LRS A10-4 (ATCC 74435)), was generated from wild-type *C. minitans* strain ATCC 74415 by UV mutagenesis and was screened for cellulase activity in the presence of glucose (whereas glucanolytic activity from the parental *C. minitans* strain ATCC 74415 was repressed in the presence of glucose). Morphological characteristics of the C minitans strains are described in International Publication No. WO 99/02662 to Huang et al.

*C. minitans* strains M11-3B 2A2, A10-4 and 2134 were inoculated into liquid potato dextrose broth ("PDB") using mycelial plugs from *C. minitans* grown on potato dextrose agar ("PDA"). Cultures were grown with constant agitation (250 rpm) at 20° C. for 14 days. Cultures were harvested after two weeks by filtration using MIRACLOTH quick-filtration material (Calbiochem, PO Box 12087, LaJolla, Calif. 92039-2087, USA, product #475855) and flash frozen in liquid nitrogen. Approximately three grams of frozen *C. minitans* mycelia was homogenized and thoroughly mixed with 20 ml of extraction buffer [100 mM Tris-HCl (pH 8.5), 100 mM NaCl, 50 mM ethylenediaminetetraacetic acid ("EDTA") (pH 8.0), 2% sodium dodecyl sulfate ("SDS") (w/v), and 0.05 mg/ml proteinase K]. The mixture was incubated at 37° C. for one hour with frequent inversion. The mixture was extracted once with 10 ml each of phenol and chloroform and precipitated with 0.6 volume of isopropanol. The genomic DNA was suspended in 0.5 ml of ultrapure water (OPTIMA, Fisher Scientific Ltd, 112 Colonnade Road, Nepean, Ontario K2E 7L6, product #W7-4) and stored at −20° C. for use as polymerase chain reaction ("PCR") template.

ii) Primer Design for PCR Amplification of a Genomic *C. minitans* Glucanase Fragment β-(1,3) exoglucanase amino acid sequences from fungal species *Ampelomyces quisqualis* (Rotem et al., 1997), *Cochliobolus carbonum* (Schaeffer et al., 1994), and *Trichoderma harzianum* (Cohen-Kupiec et al., 1999) were aligned to identify regions of homology. These three fungal species represent very divergent phylogenetic species. Two regions exhibiting stretches of homology of at least seven amino acids in length were identified. To reduce degeneracy and non-specific amplification in the PCR amplification, DNA nucleotide sequences corresponding to the two regions of homology were identified and aligned as an alternative to the construction of degenerate primers based on homologous amino acid sequences alone. Direct nucleotide sequence comparison yielded a consensus sequence that was used to generate semi-degenerate primers Gf1 (5' gg(tc)ga(tc)gg(tc) gt(tc)ac(tc)ga(tc)ga 3') SEQ ID NO: 7 and Gr1 (5' aagttgcg (ga)at(ct)tg(cg)cg 3') SEQ ID NO: 13 targeting a homologous genomic *C. minitans* glucanase fragment by PCR amplification (FIGS. 1A and 1B). The DNA sequence represented by the Gf1 and Gr1 primer pair appeared to exhibit a high level of conservation at the nucleotide level with nucleotide ambiguities (at the third nucleotide) of either AG or TC pairs (which are common ambiguities generated by transition mutations during evolution). Classical PCR amplification strategies which make use of degenerate PCR primers traditionally involve deducing nucleotide primer sequences from an amino-acid sequence based on codon usage or universal translation tables. By constructing primers using a conserved consensus nucleotide sequence from regions of high homology, the specificity with which a target sequence will be amplified is significantly increased. In this manner, the Gf1/Gr1 primer pair was designed with high specificity to the target *C. minitans* β-(1,3) exoglucanase sequence without heavy ambiguity or amplification of extraneous sequences.

iii) PCR Amplification, Cloning and Sequencing of the Genomic *C. minitans* Glucanase-Like Fragment Glu1

The PCR reactions consisted of 25 μl reactions containing 10 mM Tris-HCl (pH 8.0), 50 mM KCl, 1.5 mM $Mg^{2+}$, 0.8 mM each of primer Gf1 and Gr1, 1 U TAQ DNA POLYMERASE (Life Technologies, 8400 Helgerman Court, PO Box 6009, Gaithersburg, Md. 20898-9980, USA, product #10342-020), 0.2 mM deoxynucleotide triphosphate ("dNTP") (each of deoxyadenosine triphosphate "dATP", deoxythymidine triphosphate ("dTTP"), deoxyguanosine triphosphate ("dGTP"), and deoxycytosine triphosphate ("dCTP"), Life Technologies, product #10297-018) mix, and 150 ng of template DNA from C. minitans strains M 11-3B 2A2, A10-4 and 2134. The PCR cycle profile consisted of progressive touchdown annealing steps in which the annealing temperature decreased progressively with each cycle. After an initial denaturing step of 1.5 minutes at 94° C., the cycle consisted of: (1) a denaturing step of 1.5 minutes at 94° C; (2) an annealing step of one minute at 60° C.; and, (3) an extension step at 72° C. for two minutes. This cycle was repeated twenty times, the annealing temperature decreasing by 0.5° C. in each cycle, to a final annealing temperature of 50° C. This was followed by the same 3-step profile, annealing at 50° C., for an additional twenty cycles.

PCR reactions were resolved on a 1.5% Tris-acetate-EDTA ("TAE") agarose gel, stained with ethidium bromide, and visualized under ultraviolet ("UV") light. PCR reactions were semi-purified by passage through a 1 ml SEPHADEX G-50 DNA grade fine (Pharmacia Biotech Inc., 500 Morgan Blvd, Baie D'Urfé, Québec, Canada H9X 3V1, product #170573-01) column and ligated overnight into the pGEM-T PCR vector system (Promega Corporation, 2800 Wood Hollow Road, Madison, Wis., 53711-5399, USA, product #A3600). The ligation mix was transformed into MAX EFFICIENCY DH5α COMPETENT CELLS (Life Technologies, product #18258-012) and recombinant vectors were screened by blue-white/ampicillin selection (white LacZ-cells were indicative of recombinant clones, transformants were selected through ampicillin resistance). Plasmid DNA (pDNA) from recombinant clones was purified using the WIZARD PLUS miniprep purification system (Promega Corporation, product #A7500) and sequenced using the universal 24 base M13 forward (5' cgc cag ggt ttt ccc agt cac gac 3') SEQ ID NO: 23 and the 24 base reverse (5' agc gga taa caa ttt cac aca gga 3') SEQ ID NO: 24 sequencing primers using a fluorescent dye-terminator sequencing kit (ABI-PRISM BIGDYE TERMINATOR CYCLE SEQUENCING READY REACTION KIT, PE Applied Biosystems, 850 Lincoln Centre Drive, Foster City Calif., 94404, USA, product #4303149).

iv) Characterizing the C. minitans Glucanase-Like Genomic Fragment Sequence

Fragments of identical size and around 325 bp were observed on the agarose gel from the amplified genomic DNA originating from C. minitans strains M11-3B 2A2, A10-4 and 2134 and were cloned and sequenced. The sequence of the 319 bp genomic fragment from the three C. minitans strains M11-3B 2A2, A10-4 and 2134 was obtained from the sequenced pGEM-T clones and found to be identical. The genomic DNA sequences were entered into an alignment search algorithm (BLAST) to identify homologous sequences (Altschul et al., 1997). The C. minitans genomic fragments obtained by PCR demonstrated homology to the original C. carbonum, A. quisqualis, and T. harzianum β-(1,3) exoglucanase sequences (Schaeffer et al., 1994; Rotem et al., 1997; and Cohen-Kupiec et al., 1999) used in designing semi-degenerate primers Gf1 and Gr1. No apparent introns were observed within the glu1 genomic sequences. The absence of introns was subsequently confirmed by comparison to the full-length CBEG1 cDNA sequence.

EXAMPLE 2

Assessing Presence, Size, and Abundance of a C. minitans Glucanase-Like Hybridizing Transcript i) RNA Isolation from C. minitans Strains M11-3B 2A2, 2134 and A10-4

LRCC C. minitans strains M11-3B 2A2, 2134 and Al 0-4 were inoculated into minimal Czapek-Dox media (0.2% $NH_4H_2PO_4$, 0.1% $K_2HPO_4$, 0.05% $MgSO_4$, $7H_2O$, 0.05% KCl, 0.001% $FeSO_4$, 0.00001% $ZnSO_4$, and 0.000005% $CuSO_4$; (all w/v)) supplemented with 1% ground sclerotia of Sclerotinia sclerotiorum as the sole carbon source as well as PDB. Cultures were incubated with constant agitation (250 rpm) at 20° C. for 14 days and harvested by filtration with MIRACLOTH filtration cloth (Calbiochem). C. minitans tissue was flash frozen in liquid nitrogen and ground into a fine powder. Total RNA was extracted from ground C. minitans tissue using TRIZOL solution (Life Technologies, product #15596-018).

ii) Northern Hybridization Analysis of Total C. minitans RNA

Ten micrograms of total RNA was loaded and resolved on a 1.5% agarose gel containing 1.9% formaldehyde, and 0.02 M 3-[N-Morpholino] propanesulfonic acid ("MOPS") buffer. The RNA was transferred to a nylon membrane (MAXIMUM STRENGTH NYTRAN, Schleicher & Schuell, PO Box 2012, Keene, NH, 03431, USA, product #77404) by Northern transfer (Sambrook et al., 1989) and immobilized by UV crosslinking.

Nested primers were designed to amplify a subfragment from the C. minitans glucanase-like fragment for constructing a radiolabeled probe for hybridization to total C. minitans RNA. Primers Gf1b (5' gccatcaatgccgccatagctg 3') (nucleotides 277 to 298 of SEQ ID NO: 1) and Gr1b (5' cattggtagaagtccagcctg 3') (inverse complement sequence of nucleotides 520 to 541 of SEQ ID NO: 1) were used to PCR amplify a 265 bp C. minitans glucanase-like subfragment which was subsequently [$^{32}$P]-α-dCTP labeled by secondary PCR amplification. The radiolabeled GLU1 subfragment was hybridized to total C. minitans RNA under semi-stringent conditions [55° C. overnight in 20 ml of hybridization buffer (1% (w/v) sarkosyl, 5.8% NaCl (w/v), and 50 mM Tris-HCl (pH 7.5)), 0.4 ml of 50×Denhardt's solution (50×1% (w/v) FICOLL (Type 400, Pharmacia, product #17-0400-01), 1% (w/v) polyvinylpyrrolidone, 1% (w/v) bovine serum albumin), 10% dextran sulfate, and 20 mg of denatured herring sperm DNA] and washed under stringent conditions [two washes of 0.1×sodium chloride-sodium phosphate-EDTA ("SSPE") (20×SSPE=3.0 M NaCl, 0.2 M $NaH_2PO_4.H_2O$, 20 mM EDTA, pH 7.4), 0.1% SDS at 55° C. for 20 minutes]. The membrane was exposed to FUJI Medical X-Ray Film RX (8"×10") autoradiographic film (Innomed Christie Group Ltd., 18208 $102^{nd}$ Avenue, Edmonton, Alberta, Canada T5S1S7, product #03E050) for 12 hours at −80° C. before development.

The resulting autoradiogram indicated significant expression of a 2.3 kb transcript which hybridized to the C. minitans glucanase-like subfragment, indicating abundant expression of a glucanase-like transcript by C. minitans strains M11-3B 2A2 and 2134 when grown in presence of ground sclerotia of S. sclerotiorum as the sole carbohydrate source. This glucanase-like transcript was also present (but less abundant) in total RNA extracted from C. minitans strain A10-4 grown in presence of ground sclerotia of S. sclerotiorum. No glucanase-like-hybridizing transcript was observed in C. minitans strains 2134 (wild-type), A10-4 or M11-3B2A2 cultured in glucose-rich PDB media.

EXAMPLE 3
Constructing and Screening a *C. minitans* cDNA Library in the Isolation and Sequencing of the Full-Length Glucanase Transcript (cbeg1)

LRCC *C. minitans* strains 2134 and M11-3B2A2 were grown for 15 days on Czapek-Dox media containing 1% ground sclerotia of *S. sclerotiorum* as the sole carbohydrate source. Mycelium was collected as in Example 2, and ground in liquid nitrogen. Total RNA was extracted using TRIZOL solution (Life Technologies). Transcript RNA was purified from the total RNA mixture using a cellulose-bound oligo-dT purification system (MESSAGEMAKER mRNA Isolation System, Life Technologies, product #10551-018). First strand cDNA was synthesized from the purified mRNA using SUPERSCRIPT II RNase H⁻Reverse-Transcriptase (Life Technologies, product #18053-017) and was cloned unidirectionally into a λZAβ-cDNA GIGAPACK III GOLD cloning Kit (Stratagene, 11011 North Torrey Pines Road, La Jolla, Calif. 92037, USA, product #200450). Bacteriophage clones were packaged using X phage GIGAPACK III GOLD packaging extract (Stratagene, product #200450) and titered onto NZY agar media (1% (w/v) NZ amine, 0.5% (w/v) NaCl, 0.5% (w/v) yeast extract (Bacto), 0.2% (w/v) $MgSO_4 \cdot 7H_2O$, pH 7.0). A library was obtained from each *C. minitans* strain. Phages were plated at a density of 50,000 per plate on 15 cm Petri plates.

Nested primers Gf1b and Gr1b were used to amplify and [$^{32}$P]-αdCTP radiolabel a glucanase-like fragment by PCR from *C. minitans* genomic DNA. The radiolabeled glucanase-like fragment was used to hybridize to plaque lifts from the cDNA library at 55° C. overnight in 20 ml hybridization buffer (see Example 2) (Sambrook et al., 1989). Positive glucanase-like-hybridizing clones underwent secondary and tertiary screens. Positive tertiary clones were excised into the pBLUESCRIPT plasmid using the EXASSIST excision protocol from the λZAβ-GIGAPACK III cloning system (Stratagene, product #200450). A total of 500,000 recombinant clones were screened and five glucanase-like-hybridizing clones were identified. Following the tertiary screening of the glucanase-like-hybridizing clones, one full-length cbeg1 cDNA clone of 2677 bp originating from *C. minitans* strain 2134 with an open reading frame of 2358 bp was isolated (SEQ ID NO: 1). Both strands of the excised pBluescript clone were sequenced by primer walking using the ABI-PRISM BigDye Terminator Cycle Sequencing Ready Reaction Kit (PE Applied Biosystems, product #4303149). Sequences from both cDNA strands were found to be identical.

EXAMPLE 4
Characterization and Structural Analysis of cbeg1 cDNA by Amino Acid Sequence Alignment The Cbeg1 amino acid sequence exhibits homology with fungal β-(1,3) exoglucanases originating from *C. carbonum*, *A. quisqualis* and *T. harzianum* (FIGS. 2A–2D). Cbeg1 exhibits the greatest homology with Exg1 (*C. carbonum*) with an overall homology of 59% over the whole sequence, while the homologies of Cbeg1 are 51% with Trexo (*Trichoderma harzianum*) and 43% with ExgA (*Ampelomyces quisqualis*). Highly conserved contiguous regions of homology include a "YKVFRNVKDYGA-KGDGVTDD" motif (GAK box) extending over a stretch of 20 amino acid residues (amino acids 63 to 82 of SEQ ID NO: 2). This particular motif overlaps the "GDGVTDD" sequence targeted by the Gf1 semi-degenerate primer (amino acids 76 to 82 of SEQ ID NO: 2). A signal peptide of 21 amino acids was detected at the N-terminal end of the deduced polypeptide based on the SignalP V1.1 Server (Nielsen et al., 1997) (amino acids 1 to 21 of SEQ ID NO: 2).

Moreover, Cbeg1 exhibits 26% homology to the fungal β-(1,3)(1,4) endoglucanase bgn13.1 from the fungal mycoparasite *T. harzianum* although Cbeg1 homology to bgn13.1 fails to yield lengthy runs of conserved domains. The conserved residues between these glucanohydrolases implies that the mixed-linkage β-(1,3)(1,4) endoglucanase bgn13.1 may share a common ancestral precursor to cbeg1 and its related fungal β-(1,3) exoglucanases.

The evolution of genes within this particular gene family appear to encompass functional enzymes and proteins from a diverse variety of organisms. A conserved amino acid "GAKGDGSTDD" motif (GAX box) (amino acids 425 to 434 of SEQ ID NO: 2) appearing downstream of the above GAK box sequence exhibits homology among GAX box regions in genes of disparate enzymatic function (FIG. 3). Representative examples of genes which include derivatives of this GAK box domain include a neck appendage protein from a Bacillus bacteriophage phi-29 (Vlcek and Paces, 1986), a mannuronan C5 epimerase from the bacterial species *Azotobacter vinelandii* (Svanem et al., 1999), an endo-N-acetylneuraminidase from the bacteriophage K1F (Petter and Vimr, 1993), and an exopolygalacturonase (pectinase) from the model plant *Arabidopsis thaliana* (Torki et al., 1999). The evolutionary diversity and functional disparity of genes containing this particular conserved domain implies their derivation from an early ancestral form.

The two conserved GAK and GAX box motifs within the Cbeg1 peptide itself appear to be duplicated domains originating from a smaller ancestral precursor (FIG. 4). Sequence comparison of truncated N-terminal and C-terminal Cbeg1 sequences demonstrate conservation of key residues outside a homologous "GDGXTDD" domain (SEQ ID NO: 22). This instance of intrinsic homology may imply evolution of the functional Cbeg1 sequence through genetic duplication and variation of sequences outside this conserved region. Conservation of this "GDGXTDD" sequence within Cbeg1 and other homologous sequences of disparate origin and function denotes the significance of this domain in glucanolytic function in addition to non-glucanolytic functions evolved in genes derived from this fungal glycosyl hydrolase family.

The predicted Cbeg1 polypeptide has an isoelectric point (pI) of 6.0 and a molecular weight of 83,647 Daltons.

EXAMPLE 5
Assaying Cbeg1 Exoglucanase Activity in *Pichia pastoris* i) Subcloning and Expression of cbeg1 in the Eukaryotic System of *Pichia pastoris*

EcoRI and XbaI digestion of cbeg1 within the pBluescript (pBSK) plasmid yielded an intact cbeg1 fragment containing EcoRI and XbaI overhangs (with a short pBSK lacZ sequence upstream of the cbeg1 "atg"). The EcoRI/XbaI cbeg1 fragment was unidirectionally ligated into EcoRI/XbaI sites in the *P. pastoris* integration vector, pPICZα B (Invitrogen Corporation, 1600 Faraday Ave, Carlsbad Calif. 92008, product #K1710-01). The ligated junctions were sequenced to ensure that the resulting α-factor excretory signal peptide/cbeg1 fusion construct was in-frame.

The pPICZα B/cbeg1 integration vector was linearized by PmeI digestion and subsequently used to transform *P. pastoris* strain GS 115 spheroplasts. pPICZα B/cbeg1 integrants were selected on his⁻ regeneration dextrose base ("RDB") media (1 M sorbitol, 2% dextrose (w/v), 1.34% yeast nitrogen base (Invitrogen, product #Q300-07)(w/v), 0.00004% biotin (w/v), 0.005% amino acid mix (Invitrogen, product #Q300-18) in the presence of ZEOCIN (at 100 µg/ml) (Invitrogen, product #R250-01). Single colony integrants were selected for growth in liquid buffered minimal glycerol ("BMGH") medium (100 mM potassium phosphate, pH 6.0, 1.34% yeast nitrogen base with amonium sulfate and without amino acid (w/v) (Difco, product #DF0919-15), 0.00004% biotin (w/v), 1% glycerol (v/v)) and subsequent induction of cbeg1 expression by transfer to BMMH media (BMGH media with 0.5% methanol (v/v) substituted for glycerol). Liquid BMMH cultures were incubated 24 hours with constant agitation (250 rpm) at 30° C. Culture filtrate was collected by centrifugation and used for Cbeg1 enzyme characterization.

ii) Characterization of Secreted Cbeg1 Enzyme

The secreted Cbeg1 enzyme in transgenic *P. pastoris* culture filtrates was assayed for specific activity on varying substrates. Furthermore, pH and temperature optima were determined for the secreted enzyme. β-glucanase activity was determined by a modified reducing sugar colorimetric assay protocol (Miller, 1959). 100 µl culture filtrate was added to an equal volume of substrate solution and incubated at 37° C. The reaction was terminated by the addition of a 0.3% 3,6-dinitrophtallic acid: 1.8M $K_2CO_3$+0.1M $Na_2S_2O_3$ (1:1) solution (200 el). Chromogenic development of the reaction mix was carried out at 95° C. for 10 minutes and optical density of the reaction mixes were read at an absorbance wavelength of 490 nm using an enzyme-linked immunosorbent ("ELISA") plate reader. The specificity of the Cbeg1 enzyme in transgenic *P. pastoris* filtrates was determined by incubating culture filtrates with carboxymethylcellulose ("CMC") (Sigma, product #C-5093), barley β-glucan (Megazyme International Ireland Ltd., Bray Business Park, Bray, Co. Wicklow, Republic of Ireland, product #β-BGBM), lichenan (Sigma, product #L-6133), oat spelt xylan (Sigma, product #X-0627), birchwood xylan (Sigma, product #X-0502), and laminarin (Sigma, product #L-9634) (1% (w/v) buffered in 100 mM sodium acetate, pH 5.0) at 37° C. Protein concentration of the culture filtrates were determined using a Bradford dye reagent microassay protocol (Bio-Rad, 2000 Alfred Nobel Dr., Hercules, Calif. 94547, product 4500-0006). Culture filtrates from a non-recombinant *P. pastoris* control strain (GS 115) were assayed as a negative control. No hydrolytic activity was measured in culture filtrates derived from the *P. pastoris* control strain. Transgenic Cbeg1 culture filtrates were shown to have activity on laminarin only, producing 46 U of activity (where one unit of activity is defined as one µg of reducing sugar (glucose) liberated per hour per ml at 37° C., pH 6.5) (Table II). Induction of activity in *P. pastoris* was rapid.

pH optima was determined for *P. pastoris* filtrates by assaying laminarin hydrolysis of buffered substrates (1% (w/v) laminarin) ranging from pH 3.5 to 8 (50 mM Na acetate for pH 3.5 to 6, 50 mM $NaPO_4$ for pH 6 to 8). The pH optima for the secreted Cbeg1 enzyme was determined to be 6.0 (as a result of four assayed Cbeg1-expressing independent clones). Temperature optimum was determined by laminarin hydrolysis (1% (w/v), buffered at pH 6.5 in presence of 50 mM $NaPO_4$ buffer. Optimal glucanolytic activity occurred at a temperature of 57° C. (Table II). No activity was detected in the control *P. pastoris* media filtrates.

TABLE II

Characterization of transgenic Cxy1 expression in recombinant *Pichia pastoris* culture filtrate

| | |
|---|---|
| pH optimum | 6.0 |
| Temperature optimum | 57°C. |
| Enzymatic activity (*U): | |
| CMC | 0 |
| barley β-glucan | 0 |
| lichenan | 0 |
| laminarin | 46 |
| oat spelt xylan | 0 |
| birchwood xylan | 0 |

*one unit of catalytic activity is defined by one µg of reducing sugar (glucose) liberated at pH 6.5 and 37° C. per hour per ml of culture filtrate. This activity was measured 24 h after induction.

EXAMPLE 6

Expression of *Coniothyrium minitans* β-(1,3) Exoglucanase Gene cbeg1 in Monocots The constructs used for transformation of monocots using the bombardment technique are similar to the constructs used for the transformation of dicots, and include a promoter, the *Coniothyrium minitans* β-(1,3) exoglucanase gene cbeg1, and a terminator gene segment.

The promoter is preferably a rice actin promoter and includes the 5' terminal end of the same actin gene including the first intron (McElroy et al, 1991). A *C. minitans* β-(1,3) exoglucanase gene cbeg1 is inserted in frame and followed by a 3' non-translated fragment of the NOS gene as terminator. This construct is identified as the pCORcbeg1 construct. The bar gene conferring resistance to glufosinate ammonium is used for selection (White et al., 1990). A pMB vector, such as pMB2 or pMB4 (Erickson et al., 1999), may be used. In this vector the bar gene is inserted in frame between the 35S promoter and the NOS terminator. Equal amount of the two constructs are used to coat gold particles before their acceleration into plant tissues.

Immature scutella are dissected from embryos of the barley cultivar Golden Promise and placed on the callus induction medium. Tissues are co-transformed with the pMB4 plasmid carrying the bar marker gene and the pCORcbeg1 construct carrying the cbeg1 polynucleotide. DNA delivery to the tissues is carried out with the HELIOS Gene Gun System, a microprojectile bombardment device (Bio-Rad, product #165-2431). An equal mass of these two plasmids (25 μg each) is mixed and coated on 25 mg of 1 μm gold particles and distributed on the inside wall of a 60 cm GOLDCOAT tubing according to the manufacturer's instructions. Discharge pressure is set at 125 psi and a diffusion screen (Bio-Rad, product #165-2475) is used to ensure an even distribution of the gold particles carrying the plasmids. A similar particle delivery device, such as the Biolistic PDS-1000 He System (Bio-Rad product #165-2257), or other functionally equivalent equipment can alternatively be used. The preparation of particles and pressure used are in accordance with the manufacturer's instructions for the instrument of choice.

The scutella are transferred to callus induction medium containing 5 mg/L of glufosinate ammonium salt (Crescent Chemical, Hauppauge, NY, USA, product #C140300) 16h after bombardment. After 20–25 days, masses of cells are transferred to plant regeneration medium containing the same amount of selective agent as the previous medium. A mass of cells develops on the plant regeneration medium to produce shoots and regenerated plantlets. A mass of cells with green shoots is excised and placed on a rooting medium (without selective agent) to favour rooting. Plantlets are then transferred to soil.

Herbicide-tolerant regenerated plants are tested with the leaf brush technique (LBT) using 500 mg/L of glufosinate ammonium salt, with an abundant brushing (Wan and Lamaux, 1994).

PCR product is probed to confirm presence of the bar gene or NPTII DNA in the plant cells, and PCR and Southern blot analyses and colorimetric assays are used to confirm the presence and activity of the cbeg1 polynucleotide.

EXAMPLE 7

Expression of *Coniothyrium minitans* β-(1,3) Exoglucanase Gene cbeg1 in Dicots

A construct containing an isolated *Coniothyrium minitans* β-(1,3) exoglucanase gene cbeg1 of the invention is engineered into the pBI121 vector that contains the CaMV 35S promoter (Kay et al., 1987) and the NOS 3' terminator sequence (Bevan et al., 1983). The pBI121 plasmid is composed of the following well-characterized segments of DNA. A 0.93 kb fragment isolated from transposon Tn7 which encodes bacterial spectinomycin/streptomycin (Spc/Str) resistance and is a determinant for selection in *E. coli* and *Agrobacterium tumefaciens* (Fling et al., 1985). This is joined to a chimeric kanamycin resistance gene engineered for plant expression to allow selection of the transformed tissue. The chimeric gene consists of the 0.35 kb cauliflower mosaic virus 35S promoter (β-35S) (Odell et al., 1985), the 0.83 kb neomycin phosphotransferase type II gene (NPTII), and the 0.26 kb 3' non-translated region of the nopaline synthase gene (NOS 3,) (Fraley et al., 1983). The next segment is a 0.75 kb origin of replication from the RK2 plasmid (ori-V) (Stalker et al, 1981). It is joined to a 3.1 kb SalI to PvuI segment of pBR322 which provides the origin of replication for maintenance in *E. coli* (ori-322) and the bom site for the conjugational transfer in the Agrobacterium tumefaciens cells. Next is a 0.36 kb PvuI fragment from the pTiT37 plasmid which contains the nopaline-type T-DNA right border region (Fraley et al., 1985).

The vector containing the *C. minitans* β-(1,3) exoglucanase gene cbeg1 is transformed into the *B. napus* cultivar Westar according to the method of Moloney et al. (1989).

To prepare cotyledons for transformation, seeds are sterilized in 20% commercial bleach for 30 minutes while shaking. The seeds are then washed five times in a sterile funnel and filter paper using ddH$_2$O. The washed seeds are placed on *Brassica napus* I (BNI) seed germination medium (~20 per plate) (Moloney et al., 1989), wrapped in PARAFILM, and incubated at 25° C. for five days.

Agrobacterium harboring the plasmid of interest (e.g. pPZP (Hajdukiewicz et al., 1994) or another appropriate binary vector) is inoculated with 5 mL of Agrobacterium medium (AB) with a selection antibiotic and incubated at 28° C. for two days. Immediately prior to the transformation step, 1 mL of the Agrobacterium culture is spun down in a microfuge (13,000×g) for 1–2 minutes. The culture is resuspended in 1 mL of AB broth (no antibiotics) and diluted until OD$_{600}$=0.05.

Four to five day old cotyledons are used for transformation. The cotyledon is held with sterile forceps and cut with a sterile scalpel, without removing the apical meristem. Only a few cotyledons are cut at a time, and they are left on the germination plate to reduce dessication. The petiole of the cotyledon is dipped in the Agrobacterium suspension for 1 second and placed on BNII (co-cultivation) medium (Moloney et al, 1989). The petiole is pushed into the soft agar. To avoid growback, the cotyledon is not dipped a second time into the Agrobacterium suspension. Ten cotyledons are placed on each plate, and the plates are wrapped in PARAFILM and incubated in a growth room (25° C. with light) for two days.

The cotyledons are then transferred to BNIV (selection/regeneration) medium (Moloney et al., 1989), wrapped in PARAFILM, and incubated in a growth room. Agrobacterium growth is monitored during the first few weeks, and the tissue is transferred to new BNIV at the first sign of grow back of bacteria (approximately every second week). As soon as shoots arise from callus tissue, they are cut and placed on BNV (shoot elongation) medium (Moloney et al., 1989) in Magenta jars. Every second week, the shoots are transferred to fresh BNV medium. After the shoots have elongated, they are transferred to BNVI (rooting) medium (Moloney et al., 1989). Once the roots have formed, the plantlets are transferred to soil and placed in a misting chamber until NPTII enzymatic assays are done. NPTII positive plants are then and grown to maturity in a greenhouse growth chamber.

After enough leaf tissue has formed, Southern Blot or PCR analyses can be performed to verify presence of the *Coniothyrium minitans* β-(1,3) exoglucanase gene cbeg1. When seeds have formed, or at other stages of development, Northern, RT-PCR and Western Blots can be performed, and enzymatic activity measured.

REFERENCES

Alber, T. and Kawasaki, G. (1982) Nucleotide sequence of the triose phosphate isomerase gene of *Saccharomyces cerevisiae*. J. Mol. Appl. Genet. 1:419–434.

Atschul, S. F., Madden, T. L., Scaffer, A. A., Zhang, J., Zhang, Z., Miller, W. and Lipman, D. J. (1997) Gapped BLAST and PSI-BLAST: A new generation of protein database search programs. Nucleic Acids Res. 25:3389–3402.

Ausubel, F. M., Bent, R., Kingston, R. E., Moore, D. J., Smith, J. A., Silverman, J. G. and Struhl K. (2000) Current Protocols in Molecular Biology. John Wiley & Sons, New York.

Bachman, E. S. and McClay, D. R. (1996) Molecular cloning of the first metazoan β-1,3 glucanase from eggs of the sea urchin *Strongylocentrotus purpuratus*. Proc. Natl. Acad. Sci. 93: 6808–6813.

Bamforth, C. W. (1980) The adaptability, purification and properties of exo-β1,3-glucanase from the fungus *Trichoderma reesei*. Biochem. J. 191:863–866.

Beguin, P. and Aubert, J.-P. (1994) The biological degradation of cellulose. FEMS Microbiol Revs 13:25–58.

Bevan, M. W., Flavell, R. B. and Chilton, M.-D. (1983) A chimaeric antibiotic resistance gene as a selectable marker for plant cell transformation. Nature (London) 304:184–187.

Bevan M., Barker R., Goldsbrough, A., Jarvis, M., Kavanagh, T. and Iturriaga, G. (1986) The structure and transcription start site of a major potato tuber protein gene. Nucleic Acids Res. 14:4625–4638.

Borgia, P. T. and Dodge, C. L. (1992) Characterization of *Aspergillus nidulans* mutants deficient in cell wall chitin or glucan. J. Bacteriol. 174(2):377–383.

Breen, J. P. and Crouch, M. L. (1992) Molecular analysis of a Cruciferin storage protein gene family of *Brassica napus*. Plant Mol. Biol. 19:1049–1055.

Chen, H., Li, X.-L. and Ljungdahl, L. G. (1997) Sequencing of a 1,3-1,4-β-D-glucanase (lichenase) from the anaerobic fungus Orpinomyces strain PC-2: Properties of the enzyme expressed in *Escherichia coli* and evidence that the gene has a bacterial origin. J. Bacteriol. 179(19): 6028–6034.

Chesson, A., Forsberg, C. W. and Grenet, E. (1995) Improving the digestion of plant cell walls and fibrous feeds. In: Recent developments in the nutrition of herbivores, M. Journet, E. Grenet, M.-H. Farce, M. Theriez, C. Demarquilly (eds). Proceedings of the IVth international symposium on the nutrition of herbivores, pp. 249–277. INRA Editions, Paris.

Cho, M.-J., Jiang, W. and Lemaux, P. G. (1998) Transformation of recalcitrant barley cultivars through improvement of regenerability and decreased albinism. Plant Science 38: 229–244.

Cohen-Kupiec, R., Broglie, K. E., Friesem, D., Broglie, R. M. and Chet, I. (1999) Molecular characterization of a novel beta-1,3-exoglucanase related to mycoparasitism of *Trichoderma harzianum.* Gene 226:147–154.

Copa-Patino, J. L., Reyes, F. and Perez-Leblic, M. I. (1989) Purification and properties of a 1,3-β-glucanase from *Penicillium oxalicum* autolysates. FEMS Microbiol. Lett. 65:285–292.

de la Cruz, J., Pintor-Toro, J. A., Benitez, T., Llobell, A. and Romero, L. C. (1995) A novel endo-beta-1,3-glucanase, BGN13.1, involved in the mycoparasitism of *Trichoderma harzianum.* J. Bacteriol. 177:6937–6945.

Depicker, A., Stachel, S., Dhaese, P., Zambryski, P. and Goodman, H. M. (1982) Nopaline synthase: transcript mapping and DNA sequence *Agrobacterium tumefaciens.* J. Mol. Appl. Genet. 1:561–573.

Donzelli, B. G. G., Lorito, M., Scala, F. and Hannan, G. E. (2000) Cloning, sequence and structure of a gene encoding an antifungal glucan 1,3-beta-glucosidase from *Trichoderma atroviride* (*T. harzianum*) with a spliced regulatory sequence. GenBank accession no. AF253421.

Erickson, F. L., Holzberg, S., Calderon-Urrea, A., Handley, V., Axtell, M., Corr, C. and Baker, B. (1999) The helicase domain of the TMV replicase proteins induces the N-mediated defence response in tobacco. Plant J. 18:67–75.

Fling, M. E., Kopf, I. and Richards, C. (1985) Nucleotide sequence of the rtransposon Tn7 gene encoding an aminoglucoside-modifying enzyme 3"(9)-O-nucleotidyltransferase. Nucleic Acids Res. 13: 7095–7106.

Fraley, R. T., Rogers, S. G., Horsch, R. B., Sanders, P. R. and Flick, J. S. (1983) Expression of bacterial genes in plant cells *Agrobacterium tumefaciens.* Proc. Natl. Acad. Sci. USA 80:4803–4807.

Fraley, R. T., Rogers, S. G., Horsch, R. B., Eichholtz, D. A., Flick, J. S, Fink, C. L., Hoffmann, N. L. and Sanders, P. R. (1985) The SEV system: a new disarmed Ti plasmid vector system for plant transformation. Bio/Technology 3:629–635.

Gelvin, S. B., Schilperoort, R. A. and Verma, D. P. S. (1994) Plant Molecular Biology Manual. Kluwer Academic Publishers. Belgium.

Giczey, G., Kerenyi, Z. and Hornok, L. (2000) Isolation and characterization of a beta-1,3-glucanase gene from the mycoparasite *Coniothyrium minitans.* Genbank accession no. AF247649.

Gielen, J., De Beuckeleer, M., Seurinck, J., Deboeck, F. and De Greve, H. (1984) The complete nucleotide sequence of the TL-DNA of the *Agrobacterium tumefaciens* plasmid pTiAch5. EMBO J. 3:835–846.

Hajdukiewicz, P., Svab, Z. and Maliga, P. (1994) The small, versatile pPZP family of Agrobacterium binary vectors for plant transformation. Plant Mol. Biol. 25: 989–994.

Henrissat, B. Claeyssens, M., Tomme, P., Lemesle, L. and Mornon, J.-P. (1989) Cellulase families revealed by hydrophobic cluster analysis. Gene 81:83–95.

Henrissat, B. and Bairoch, A. (1993) New families in the classification of glycosyl hydrolases based on amino acid sequence similiarities. Biochem. J. 293: 781–788.

Hoj, P. B. and Fincher, G. B. (1995) Molecular evolution of plant, β-glucan endohyrolases. Plant J. 7(3):367–379.

Huang, H. C. and Hoes, J. A. (1976) Penetration and infection of *Sclerotinia sclerotiorum* by *Coniothyrium minitans.* Can. J. Bot. 54:2843–2489.

Huang, H. C. and Kokko, E. G. (1987) Ultrastructure of hyperparasitism of *Coniothyrium minitans* on sclerotia of *Sclerotinia sclerotiorum.* Can. J. Bot. 65:2843–2489.

Huang, H. C. and Kokko, E. G. (1988) Penetration of hyphae of *Sclerotinia sclerotiorum* by *Coniothyrium minitans* without the formation of appressoria. Phytopath. Zeit. 123:133–139.

Jones, D., Gordon, A. H. and Bacon, J. S. D. (1974) Co-operative action by endo- and exo-β-(1,3)-glucanases from parasitic fungi in the degradation of cell-wall glucans of *Sclerotinia sclerotiorum* (Lib.) de Bary. Biochem. J. 140:47–55.

Kay, R., Chan, A., Daly, M. and McPherson, J. (1987) Duplication of CaMV 35S orimoter sequences creates a strong enhancer for plant genes. Science 236:1299–1302.

McElroy, D., Blowers, A. D., Jenes, B. and Wu, R. (1991) Construction of expression vectors based on the rice actin 1 (Act1) 5' region for use in monocot transformation. Mol. Gen. Genet. 231:150–160.

Miller, G. L. (1959) Use of dinitrosalicylic acid reagent for determination of reducing sugars. Anal. Chem. 31:426–428.

Moloney, M. M., Walker, J. M. and Sharma, K. K. (1989) High efficiency transformation of *Brassica napus* using Agrobacterium vectors. Plant Cell Reports 8:238–242.

Nielsen, H., J. Engelbrecht, S. Brunak, and G. V. Heijne. (1997) Identification of prokaryotic and eukaryotic signal peptides and prediction of their cleavage sites. Prot. Eng. 10:1–6.

Odell, J. T., Nagy, F. and Chua, N.-H. (1985) Identification of DNA sequences required for activity of the cauliflower mosaic virus 35S promoter. Nature 313:810–812.

Peberdy, J. F. (1990) Fungal cell wall—a review. In: Biochemistry of cell walls and membranes in fungi, P. J. Kuhn, A. P. J. Trinci, M. J. Jung, M. W. Goosey and L. G. Cooping (eds.), pp. 5–24.

Petter J. G., and Vimr, E. R. (1993) Complete nucleotide sequence of the bacteriophage K1F tail gene encoding endo-N-acylneuraminidase (endo-N) and comparison to an endo-N homolog in bacteriophage PK1E. J. Bacteriol. 175(14):4354–4363.

Rotem, Y., Yarden, O. and Sztejnberg, A. (1997) The mycoparasite *Ampelomyces quisqualis* express several exo-beta-1,3-glucanases in culture and during mycoparasitism. GenBank accession no. AF029354.

Sambrook, J., Fritsch, E. F. and Maniatis, T. (1989) Molecular Cloning, A Laboratory Manual. Cold Spring Harbour Laboratory Press.

Schaeffer, H. J., Leykam, J. and Walton, J. D. (1994) Cloning and targeted gene disruption of EXG1, encoding exo-beta 1,3-glucanase, in the phytopathogenic fungus *Cochliobolus carbonum.* Appl. Environ. Microbiol. 60(2):594–598.

Scofield. S. R. and Crouch. M. L. (1987) Nucleotide sequence of a member of the napin storage protein family from *Brassica napus.* J. Biochem. 262:12202–12208.

Stahmann, K.-P., Schimz, K.-L. and Sahm, H. (1993) Purification and characterization of four extracellular 1,3-β-glucanases of *Botrytis cinerea.* J. Gen. Microbiol. 139:2833–2840, Stalker, D. M., Thomas, C. M. and Helinski, D. R. (1981) Nucleotide sequence of the region of the origin of replication of the broad host range plasmid RK2. Mol. Gen. Genet. 181:8–12.

Svanem, B. I. G., Skjaak-Braek, G., Ertesvaag, H. and Valla, S. (1999) Cloning and expression of three new *Azotobacter vinelandii* genes closely related to a previously described gene family encoding mannuronan C-5-epimerases. J. Bacteriol. 181(1):68–77, Teather, R. M. and Erfle, J. D. (1990) DNA sequence of a *Fibrobacter succinogenes* mixed-linkage beta-glucanase (1,3-1,4-beta-D-glucan 4-glucanohydrolase) gene. J. Bacteriol. 172(7): 3837–3841.

Thomson, J. A. (1993) Molecular biology of xylan degradation-FEMS Microbiol. Rev. 104: 65–82.

Tingay, S., McElroy, D-, Kalla, R., Fieg, S. Wang, M., Thornton, S. and Brettell, R. (1997) *Agrobacierium tumefaciens*-mediated barley transformation. Plant J. 11:1369–1376.

Torki, M., Mandaron, P, Thomas, F., Quigley, F., Mache, R. and Falconet, D. (1999) Differential expression of a polygalacturonase gene family in *Arabidopsis thaliana*. Mol. Gen. Genet. 2261(6): 948–952.

Trick, H. N. and Finer, J. J. (1997) SAAT: sonication-assisted Agrobacterium-mediated transformation. Transgenic Res. 6:329–336.

Umemoto, N., Kakitani, M., Iwamatsu, A., Yoshikawa, M., Yamaoka, N. and Ishida, I. (1997) The structure and function of a soybean β-glucan-elicitor-binding protein. Proc. Natl. Acad. Sci. 94:1029–1034.

Vazquez-Garciduenas, S., Leal-Morales, C. A. and Herrera-Estrella, A. (1998) Analysis of the β-1,3-glucanolytic system of the biocontrol agent *Trichoderma hazarium*. Appl. Environ. Microbiol. 64(4):1442–1446.

Vlcek, C. and Paces, V. (1986) Nucleotide sequence of the late region of *Bacillus phage* phi-29 completes the 19285-bp sequence of phi-29 genome: comparison with the homologous sequence of phage PZA. Gene 46:215–225.

Wan, Y. and Lemaux, P. G. (1994) Generation of large numbers of independently transformed fertile barley plants Plant Physiol. 104:37–48.

Weeks, J. T., Anderson, O. D. and Blechl, A. L. (1993) Rapid production of multiple independent lines of fertile transgenic wheat (*Triticum aesivum*). Plant Physiol. 102:1077–1084.

White, J., Chang, S. Y., Bibb, M. J. and Bibb, M .J. (1990) A casssette containing the bar gene of *Streptomyces hygroscopious*: a selectable marker for plant transformation. Nucleic Acids Res. 18.1062.

Wolf, M., Geczi, A-, Simon, O. and Borriss, R. (1995) Genes encoding xylan and beta-glucan hydrolysing enzymes in *Bacillus subtilis*: characterization, mapping and construction of strains deficient in lichenase, cellulase and xylanase. Microbiology 141(2):291-290.

PATENT DOCUMENTS

Huang, H. C., Cheng, K.-J, Zantinge, J. and Laroche, A. (1998) Strains of *Coniothyrium minitans* having 1,3 and 1,4 beta-glucanase activity. International Publication No-WO 99/02662.

Swanson, R. V., Feldman, R. A. and Schleper, C. (2000) Nucleic acids and proteins from *Cenarchaeum symbiosum*, International Publication No. WO 00/18909.

All publications mentioned in this specification are indicative of the level of skill in the art to which this invention pertains. All publications are herein incorporated by reference to the same extent as if each individual publication was specifically and individually indicated to be incorporated by reference.

Although the foregoing invention has been described in some detail by way of illustration and example, for purposes of clarity and understanding it will be understood that certain changes and modifications may be made without departing from the scope or spirit of the invention as defined by the following claims.

What is claimed is:

1. An isolated nucleic acid encoding a polypeptide possessing β-(1,3) exoglucanase activity, said encoded polypeptide selected from the group consisting of:
   a) the amino acid sequence depicted in SEQ ID NO:2 from amino acid 1 to amino acid 785; and
   b) the amino acid sequence depicted in SEQ ID NO:2 from amino acid 22 to amino acid 785.

2. The isolated nucleic acid according to claim 1, said nucleic acid comprising the nucleotide sequence depicted in SEQ ID NO:1 from nucleotide 25 to nucleotide 2379.

3. The isolated nucleic acid according to claim 1, said nucleic acid comprising the nucleotide sequence depicted in SEQ ID NO:1 from nucleotide 1 to nucleotide 2677.

4. A vector comprising the nucleic acid according to claim 1.

5. A cell other than *Coniothyrium minitans*, comprising the nucleic acid according to claim 1.

6. A method for producing a transgenic plant wherein the method comprises the steps of:
   a) introducing the nucleic acid of claim 1 into plant cells of by means selected from the group consisting of particle bombardment, Agrobacterium-mediated transformation, and viral infection;
   b) selecting for the transformed plant cells by culturing the plant cells in a selective medium;
   c) culturing the transformed plant cells in media to support regeneration of the transformed plant cells to produce the transgenic plant; and
   d) confirming expression of the nucleic acid in the transgenic plant by means selected from the group consisting of polymerase chain reaction and Southern blot analyses.

7. The method according to claim 6, wherein the plant is selected from the group consisting of Brassica, Linum, *Zea mays*, Glycine, Soja, Gossypium, *Arabidopsis thaliana*, Triticum, Secale, Hordeum, Avena, Oryza, Sorghum, Solanum, Lycopersicon, Nicotiana and Cucurbita.

8. An isolated nucleic acid encoding a polypeptide possessing β-(1,3) exoglucanase activity, wherein said polypeptide is at least 90% identical to the amino acid sequence depicted in SEQ ID NO:2.

9. The isolated nucleic acid according to claim 8, wherein said encoded polypeptide comprises an amino acid sequence having at least 95% identity with the amino acid sequence depicted in SEQ ID NO:2.

10. The isolated nucleic acid according to claim 8, said nucleic acid comprising a nucleotide sequence having at least 95% identity with the nucleotide sequence depicted in SEQ ID NO:1.

* * * * *

SEQUENCE LISTING

```
<160> NUMBER OF SEQ ID NOS: 24

<210> SEQ ID NO 1
<211> LENGTH: 2677
<212> TYPE: DNA
<213> ORGANISM: Coniothyrium minitans
<220> FEATURE:
<221> NAME/KEY: CDS
<222> LOCATION: (25)..(2382)
<220> FEATURE:
<221> NAME/KEY: sig_peptide
<222> LOCATION: (25)..(87)
<220> FEATURE:
<223> OTHER INFORMATION: cbeg1

<400> SEQUENCE: 1
gcatcgtcaa ctgcgtctgg catc atg cgt tta ctt tcc ttc ttt tcc tgc      51
                         Met Arg Leu Leu Ser Phe Phe Ser Cys
                           1               5 ctg ctg gca gcg gga ggc cct gca tct gcc ctg gcc tta cct tca ccc     99
Leu Leu Ala Ala Gly Gly Pro Ala Ser Ala Leu Ala Leu Pro Ser Pro
 10              15                  20                  25 atc gca aac gac gct acg agt gct ccc ctc gag gaa cgc cag gca agt    147
Ile Ala Asn Asp Ala Thr Ser Ala Pro Leu Glu Glu Arg Gln Ala Ser
```

```
                    30                    35                   40
tca tac tgg ctg gag aac att cag cat cag ggc cgt gca gcc ttc aac       195
Ser Tyr Trp Leu Glu Asn Ile Gln His Gln Gly Arg Ala Ala Phe Asn
                    45                   50                 55 gct aac ccg gct ggc tac aaa gta ttt cga aat gtc aag gac tac ggg       243
Ala Asn Pro Ala Gly Tyr Lys Val Phe Arg Asn Val Lys Asp Tyr Gly
            60                  65                  70 gca aag ggc gat ggt gtc act gac gac tca gcc gcc atc aat gcc gcc       291
Ala Lys Gly Asp Gly Val Thr Asp Asp Ser Ala Ala Ile Asn Ala Ala
        75                  80                  85 ata gct gat ggc aac cgc tgc gct ccg tgg gta tgc gat tcc tct aca       339
Ile Ala Asp Gly Asn Arg Cys Ala Pro Trp Val Cys Asp Ser Ser Thr
    90                  95                 100                 105 gat act cct gcc atc gtc tac ttt ccc agt ggc aca tat gtc atc gga       387
Asp Thr Pro Ala Ile Val Tyr Phe Pro Ser Gly Thr Tyr Val Ile Gly
                   110                 115                 120 aag ccg atc atc atg tac tac atg aca cag ctt cac gga aac ccc aac       435
Lys Pro Ile Ile Met Tyr Tyr Met Thr Gln Leu His Gly Asn Pro Asn
               125                 130                 135 aac cgc cca gtg ctc aag gcc tcg cca aat cta cga gct ata gca ttg       483
Asn Arg Pro Val Leu Lys Ala Ser Pro Asn Leu Arg Ala Ile Ala Leu
           140                 145                 150 atc gat gcc agt ccc tat cag gat ggc acg gga aaa cca ggc tgg act       531
Ile Asp Ala Ser Pro Tyr Gln Asp Gly Thr Gly Lys Pro Gly Trp Thr
155                 160                 165 tct acc aat gtt ttt acc cgg cag att cgg aac ttt gtg atc gac ttg       579
Ser Thr Asn Val Phe Thr Arg Gln Ile Arg Asn Phe Val Ile Asp Leu
170                 175                 180                 185 acc ccg atc cca gca acc agc ggc gct cag ggt atc cat tgg cca gct       627
Thr Pro Ile Pro Ala Thr Ser Gly Ala Gln Gly Ile His Trp Pro Ala
                    190                 195                 200 tct cag gcg acc agc atc cag gat gtc aag att cag atg aat gtt gct       675
Ser Gln Ala Thr Ser Ile Gln Asp Val Lys Ile Gln Met Asn Val Ala
                205                 210                 215 gca aac tca gta cat gtt ggt atc ttt atc gag aac ggt tcc ggg gga       723
Ala Asn Ser Val His Val Gly Ile Phe Ile Glu Asn Gly Ser Gly Gly
            220                 225                 230 cat ctt act gac atc gag act gtg ggt ggt ttg cac gga ctc aat gtc       771
His Leu Thr Asp Ile Glu Thr Val Gly Gly Leu His Gly Leu Asn Val
        235                 240                 245 ggc aat cag cag ttc acc atg aag aac atc gtg atc tca aat gct gtc       819
Gly Asn Gln Gln Phe Thr Met Lys Asn Ile Val Ile Ser Asn Ala Val
250                 255                 260                 265 gtc ggt atc aac cag atc tgg aat tgg ggc tgg tta tgg aag ggt ctt       867
Val Gly Ile Asn Gln Ile Trp Asn Trp Gly Trp Leu Trp Lys Gly Leu
                    270                 275                 280 acc atc agc gac tgc agc acc gcc gct ttc tcg atg aag agt ctc aaa       915
Thr Ile Ser Asp Cys Ser Thr Ala Ala Phe Ser Met Lys Ser Leu Lys
                285                 290                 295 gac aac agt cct gat cag aac gtc gca tcg gta atc atc att gac agc       963
Asp Asn Ser Pro Asp Gln Asn Val Ala Ser Val Ile Ile Ile Asp Ser
            300                 305                 310 act atc acc aac tgt ccg att ttt gta gac tca gct tgg act agg act      1011
Thr Ile Thr Asn Cys Pro Ile Phe Val Asp Ser Ala Trp Thr Arg Thr
        315                 320                 325 tca acc gcg gcc gga tcc gga cag ctc atc ttg gaa aac att gct ctg      1059
Ser Thr Ala Ala Gly Ser Gly Gln Leu Ile Leu Glu Asn Ile Ala Leu
330                 335                 340                 345 aat aat gtt ccc gtt gcg gtt aag gga ccc agc gga aca gtt ctt gcg      1107
```

-continued

```
Asn Asn Val Pro Val Ala Val Lys Gly Pro Ser Gly Thr Val Leu Ala
            350                 355                 360 ggc ggt acc acg act atc gcg ggc tgg ggc caa ggc aac cag tac acc    1155
Gly Gly Thr Thr Thr Ile Ala Gly Trp Gly Gln Gly Asn Gln Tyr Thr
        365                 370                 375 cct ggt ggt cca act aag ttt caa ggt gca atc act cct gtg cgt ccg    1203
Pro Gly Gly Pro Thr Lys Phe Gln Gly Ala Ile Thr Pro Val Arg Pro
    380                 385                 390 gct ggc ctc ctt gat ggt aag aac ttc tac gcc aag tcg aag cct cag    1251
Ala Gly Leu Leu Asp Gly Lys Asn Phe Tyr Ala Lys Ser Lys Pro Gln
395                 400                 405 tac gaa acc gtc gcg gtc ggt aac ttc gta agt gca cgt act tct ggg    1299
Tyr Glu Thr Val Ala Val Gly Asn Phe Val Ser Ala Arg Thr Ser Gly
410                 415                 420                 425 gct aag ggc gac gga agc acc gac gat acc act gcg ctc cag aac gcg    1347
Ala Lys Gly Asp Gly Ser Thr Asp Asp Thr Thr Ala Leu Gln Asn Ala
                430                 435                 440 atc aac tct gtt gct tct tcc ggc aag atc ctc ttc ctg gac cat ggt    1395
Ile Asn Ser Val Ala Ser Ser Gly Lys Ile Leu Phe Leu Asp His Gly
            445                 450                 455 cat tac aaa att acc aag aca ctc tac ctt cct cct ggg acg aag atc    1443
His Tyr Lys Ile Thr Lys Thr Leu Tyr Leu Pro Pro Gly Thr Lys Ile
        460                 465                 470 gtt ggc gag aca tat ccc atc atc ttg gca agc ggc agc act tgg aac    1491
Val Gly Glu Thr Tyr Pro Ile Ile Leu Ala Ser Gly Ser Thr Trp Asn
    475                 480                 485 agc aaa acg aac ccc gtg ccg gtc gtc cag gtt ggc aag gct ggc gag    1539
Ser Lys Thr Asn Pro Val Pro Val Val Gln Val Gly Lys Ala Gly Glu
490                 495                 500                 505 agt ggc agc gtt gag tta tct gac ttc ctg att ggt acc caa ggg cct    1587
Ser Gly Ser Val Glu Leu Ser Asp Phe Leu Ile Gly Thr Gln Gly Pro
                510                 515                 520 acc ccc ggt gcg aag ctg atc gaa tac aac atg gcc act act aag ggc    1635
Thr Pro Gly Ala Lys Leu Ile Glu Tyr Asn Met Ala Thr Thr Lys Gly
            525                 530                 535 tct ggt atg tgg gat gtc cat acc cgt atc ggt ggt gcg aaa gga acc    1683
Ser Gly Met Trp Asp Val His Thr Arg Ile Gly Gly Ala Lys Gly Thr
        540                 545                 550 aac ctc cag gtc gct cag tgt ccc gtt ggt agt gtc aac gat gct tgc    1731
Asn Leu Gln Val Ala Gln Cys Pro Val Gly Ser Val Asn Asp Ala Cys
    555                 560                 565 atg gct gcc cac acc aac gtc cac atc acg aag agc gcg aac aac gtc    1779
Met Ala Ala His Thr Asn Val His Ile Thr Lys Ser Ala Asn Asn Val
570                 575                 580                 585 tac atg gag aac aac tgg ttt tgg acc gcg gac cac gat ctc gat gac    1827
Tyr Met Glu Asn Asn Trp Phe Trp Thr Ala Asp His Asp Leu Asp Asp
                590                 595                 600 tct gtt agc act cag atc tcc atc ttc gtc ggc cga ggt ctt ctc gtc    1875
Ser Val Ser Thr Gln Ile Ser Ile Phe Val Gly Arg Gly Leu Leu Val
            605                 610                 615 gag ggc acc aac att tgg cta tat ggc aac gga gcg gaa cac cag tct    1923
Glu Gly Thr Asn Ile Trp Leu Tyr Gly Asn Gly Ala Glu His Gln Ser
        620                 625                 630 ttg tac caa tac cag ttc gcg aac gcc aaa gac gtc ttt gca ggc ttc    1971
Leu Tyr Gln Tyr Gln Phe Ala Asn Ala Lys Asp Val Phe Ala Gly Phe
    635                 640                 645 atc cag agc gag acc cca tat tac atg ccc aca ccg gat gct aag agt    2019
Ile Gln Ser Glu Thr Pro Tyr Tyr Met Pro Thr Pro Asp Ala Lys Ser
650                 655                 660                 665
```

-continued

```
cag ccg tac cct gtg aac agc gcc ctc aat gac ccc gac tac aac acc    2067
Gln Pro Tyr Pro Val Asn Ser Ala Leu Asn Asp Pro Asp Tyr Asn Thr
                670                 675                 680 att tgc ccc tct ggc caa cgt tgc gac gca ctt gga ctg cgc gtg ctg    2115
Ile Cys Pro Ser Gly Gln Arg Cys Asp Ala Leu Gly Leu Arg Val Leu
            685                 690                 695 aac tcg tca aac gtc ctc ctc tac ggc gaa ggc ttc tat tcc ttc ttc    2163
Asn Ser Ser Asn Val Leu Leu Tyr Gly Glu Gly Phe Tyr Ser Phe Phe
        700                 705                 710 atc tcc aac aac aac tcg tgc agc aag aac acc aac tct gtt cgc gac    2211
Ile Ser Asn Asn Asn Ser Cys Ser Lys Asn Thr Asn Ser Val Arg Asp
    715                 720                 725 tgc cag aac cgc atg gtc agc atc gaa ggc tcg tcg acg gtc cgc gca    2259
Cys Gln Asn Arg Met Val Ser Ile Glu Gly Ser Ser Thr Val Arg Ala
730                 735                 740                 745 tac tcg ctg aac gaa gtc ggc gcg ctg cag atg ctc acc gtt gat ggc    2307
Tyr Ser Leu Asn Glu Val Gly Ala Leu Gln Met Leu Thr Val Asp Gly
                750                 755                 760 gtg gac aag gca gat tgg atg cct aat cta tct ggc tat gcc aac acc    2355
Val Asp Lys Ala Asp Trp Met Pro Asn Leu Ser Gly Tyr Ala Asn Thr
            765                 770                 775 att ggg tac ttt tca tac aac atc tag agatgatatg cctggctaga          2402
Ile Gly Tyr Phe Ser Tyr Asn Ile
        780                 785 gcattgttag gctccatctg ggtagatgta ttctttctac tgtatatact tgcggctttg  2462
ggaatacggc ggcggcgggt ccttgtacgt aggccgtatt tttcgctttt actttggaat  2522
atctaggatt taaattgcat acgtgacggt aaggtgtcgg atggtttttg gcttggctgg  2582
ggggatgcgg gtggttggag ggtagtgaat agaaagtacc cttgtcaaaa aaaaaaaaaa  2642
aaaaaaaaaa aaaaaaaaaa aaaaaaaaaa aaaaa                             2677

<210> SEQ ID NO 2
<211> LENGTH: 785
<212> TYPE: PRT
<213> ORGANISM: Coniothyrium minitans
<220> FEATURE:
<223> OTHER INFORMATION: cbeg1

<400> SEQUENCE: 2

Met Arg Leu Leu Ser Phe Phe Ser Cys Leu Leu Ala Ala Gly Gly Pro
  1               5                  10                  15

Ala Ser Ala Leu Ala Leu Pro Ser Pro Ile Ala Asn Asp Ala Thr Ser
             20                  25                  30

Ala Pro Leu Glu Glu Arg Gln Ala Ser Ser Tyr Trp Leu Glu Asn Ile
         35                  40                  45

Gln His Gln Gly Arg Ala Ala Phe Asn Ala Asn Pro Ala Gly Tyr Lys
     50                  55                  60

Val Phe Arg Asn Val Lys Asp Tyr Gly Ala Lys Gly Asp Gly Val Thr
 65                  70                  75                  80

Asp Asp Ser Ala Ala Ile Asn Ala Ala Ile Ala Asp Gly Asn Arg Cys
                 85                  90                  95

Ala Pro Trp Val Cys Asp Ser Ser Thr Asp Thr Pro Ala Ile Val Tyr
            100                 105                 110

Phe Pro Ser Gly Thr Tyr Val Ile Gly Lys Pro Ile Ile Met Tyr Tyr
        115                 120                 125

Met Thr Gln Leu His Gly Asn Pro Asn Asn Arg Pro Val Leu Lys Ala
    130                 135                 140
```

```
Ser Pro Asn Leu Arg Ala Ile Ala Leu Ile Asp Ala Ser Pro Tyr Gln
145                 150                 155                 160

Asp Gly Thr Gly Lys Pro Gly Trp Thr Ser Thr Asn Val Phe Thr Arg
            165                 170                 175

Gln Ile Arg Asn Phe Val Ile Asp Leu Thr Pro Ile Pro Ala Thr Ser
            180                 185                 190

Gly Ala Gln Gly Ile His Trp Pro Ala Ser Gln Ala Thr Ser Ile Gln
            195                 200                 205

Asp Val Lys Ile Gln Met Asn Val Ala Ala Asn Ser Val His Val Gly
210                 215                 220

Ile Phe Ile Glu Asn Gly Ser Gly His Leu Thr Asp Ile Glu Thr
225                 230                 235                 240

Val Gly Gly Leu His Gly Leu Asn Val Gly Asn Gln Gln Phe Thr Met
                245                 250                 255

Lys Asn Ile Val Ile Ser Asn Ala Val Val Gly Ile Asn Gln Ile Trp
            260                 265                 270

Asn Trp Gly Trp Leu Trp Lys Gly Leu Thr Ile Ser Asp Cys Ser Thr
            275                 280                 285

Ala Ala Phe Ser Met Lys Ser Leu Lys Asp Asn Ser Pro Asp Gln Asn
290                 295                 300

Val Ala Ser Val Ile Ile Ile Asp Ser Thr Ile Thr Asn Cys Pro Ile
305                 310                 315                 320

Phe Val Asp Ser Ala Trp Thr Arg Thr Ser Thr Ala Ala Gly Ser Gly
                325                 330                 335

Gln Leu Ile Leu Glu Asn Ile Ala Leu Asn Asn Val Pro Val Ala Val
            340                 345                 350

Lys Gly Pro Ser Gly Thr Val Leu Ala Gly Gly Thr Thr Ile Ala
        355                 360                 365

Gly Trp Gly Gln Gly Asn Gln Tyr Thr Pro Gly Gly Pro Thr Lys Phe
        370                 375                 380

Gln Gly Ala Ile Thr Pro Val Arg Pro Ala Gly Leu Leu Asp Gly Lys
385                 390                 395                 400

Asn Phe Tyr Ala Lys Ser Lys Pro Gln Tyr Glu Thr Val Ala Val Gly
            405                 410                 415

Asn Phe Val Ser Ala Arg Thr Ser Gly Ala Lys Gly Asp Gly Ser Thr
            420                 425                 430

Asp Asp Thr Thr Ala Leu Gln Asn Ala Ile Asn Ser Val Ala Ser Ser
            435                 440                 445

Gly Lys Ile Leu Phe Leu Asp His Gly His Tyr Lys Ile Thr Lys Thr
450                 455                 460

Leu Tyr Leu Pro Pro Gly Thr Lys Ile Val Gly Glu Thr Tyr Pro Ile
465                 470                 475                 480

Ile Leu Ala Ser Gly Ser Thr Trp Asn Ser Lys Thr Asn Pro Val Pro
                485                 490                 495

Val Val Gln Val Gly Lys Ala Gly Glu Ser Gly Ser Val Glu Leu Ser
                500                 505                 510

Asp Phe Leu Ile Gly Thr Gln Gly Pro Thr Pro Gly Ala Lys Leu Ile
            515                 520                 525

Glu Tyr Asn Met Ala Thr Thr Lys Gly Ser Gly Met Trp Asp Val His
            530                 535                 540

Thr Arg Ile Gly Gly Ala Lys Gly Thr Asn Leu Gln Val Ala Gln Cys
545                 550                 555                 560

Pro Val Gly Ser Val Asn Asp Ala Cys Met Ala Ala His Thr Asn Val
```

```
                  565                 570                 575
His Ile Thr Lys Ser Ala Asn Val Tyr Met Glu Asn Asn Trp Phe
            580                 585                 590

Trp Thr Ala Asp His Asp Leu Asp Asp Ser Val Ser Thr Gln Ile Ser
            595                 600                 605

Ile Phe Val Gly Arg Gly Leu Leu Val Glu Gly Thr Asn Ile Trp Leu
    610                 615                 620

Tyr Gly Asn Gly Ala Glu His Gln Ser Leu Tyr Gln Tyr Gln Phe Ala
625                 630                 635                 640

Asn Ala Lys Asp Val Phe Ala Gly Phe Ile Gln Ser Glu Thr Pro Tyr
                645                 650                 655

Tyr Met Pro Thr Pro Asp Ala Lys Ser Gln Pro Tyr Pro Val Asn Ser
            660                 665                 670

Ala Leu Asn Asp Pro Asp Tyr Asn Thr Ile Cys Pro Ser Gly Gln Arg
            675                 680                 685

Cys Asp Ala Leu Gly Leu Arg Val Leu Asn Ser Ser Asn Val Leu Leu
690                 695                 700

Tyr Gly Glu Gly Phe Tyr Ser Phe Phe Ile Ser Asn Asn Ser Cys
705                 710                 715                 720

Ser Lys Asn Thr Asn Ser Val Arg Asp Cys Gln Asn Arg Met Val Ser
                725                 730                 735

Ile Glu Gly Ser Ser Thr Val Arg Ala Tyr Ser Leu Asn Glu Val Gly
            740                 745                 750

Ala Leu Gln Met Leu Thr Val Asp Gly Val Asp Lys Ala Asp Trp Met
            755                 760                 765

Pro Asn Leu Ser Gly Tyr Ala Asn Thr Ile Gly Tyr Phe Ser Tyr Asn
    770                 775                 780

Ile
785

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence:amino acid
      consensus sequence for PCR forward primer Gf1

<400> SEQUENCE: 3

Lys Gly Asp Gly Val Thr Asp Asp Thr Ala
  1               5                  10

<210> SEQ ID NO 4
<211> LENGTH: 30
<212> TYPE: DNA
<213> ORGANISM: Ampelomyces quisqualis
<300> PUBLICATION INFORMATION:
<308> DATABASE ACCESSION NUMBER: GenBank accession No. AF029354
<309> DATABASE ENTRY DATE: 1998-04-02

<400> SEQUENCE: 4
aagggcgacg gcgttaccga tgacaccgct                                      30

<210> SEQ ID NO 5
<211> LENGTH: 21
<212> TYPE: DNA
<213> ORGANISM: Cochliobolus carbonum
<300> PUBLICATION INFORMATION:
<308> DATABASE ACCESSION NUMBER: Genbank accession No. L48994
<309> DATABASE ENTRY DATE: 1995-11-21
```

```
<400> SEQUENCE: 5
ggtgacggtg tcactgacga c                                              21

<210> SEQ ID NO 6
<211> LENGTH: 24
<212> TYPE: DNA
<213> ORGANISM: Trichoderma harzianum
<300> PUBLICATION INFORMATION:
<308> DATABASE ACCESSION NUMBER: GenBank accession No. AJ002397
<309> DATABASE ENTRY DATE: 1997-11-21

<400> SEQUENCE: 6
ggtgatggtg ttaccgacga cacg                                           24

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:PCR
      semi-degenerate primer Gf1

<400> SEQUENCE: 7
ggygayggyg tyacygayga                                                20

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence:amino acid
      consensus sequence of PCR reverse primer Gr1

<400> SEQUENCE: 8

Arg Gln Ile Arg Asn Phe Val
  1               5

<210> SEQ ID NO 9
<211> LENGTH: 21
<212> TYPE: DNA
<213> ORGANISM: Ampelomyces quisqualis
<300> PUBLICATION INFORMATION:
<308> DATABASE ACCESSION NUMBER: GenBank accession No. AF029354
<309> DATABASE ENTRY DATE: 1998-04-02

<400> SEQUENCE: 9
cgccagattc gcaacttcgt c                                              21

<210> SEQ ID NO 10
<211> LENGTH: 18
<212> TYPE: DNA
<213> ORGANISM: Cochliobolus carbonum
<300> PUBLICATION INFORMATION:
<308> DATABASE ACCESSION NUMBER: GenBank Accession No. L48994
<309> DATABASE ENTRY DATE: 1995-11-21

<400> SEQUENCE: 10
cgccaaatcc gcaacttg                                                  18

<210> SEQ ID NO 11
<211> LENGTH: 21
<212> TYPE: DNA
<213> ORGANISM: Trichoderma harzianum
<300> PUBLICATION INFORMATION:
<308> DATABASE ACCESSION NUMBER: GenBank accession No. AJ002397
<309> DATABASE ENTRY DATE: 1997-11-21
```

<400> SEQUENCE: 11
cggcaagtcc gcaactttaa g         21

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence:consensus
      sequence

<400> SEQUENCE: 12
cgscaratyc gcaactt         17

<210> SEQ ID NO 13
<211> LENGTH: 17
<212> TYPE: DNA
<213> ORGANISM: Artificial Sequence
<220> FEATURE:
<223> OTHER INFORMATION: Description of Artificial Sequence:PCR reverse
      semi-degenerate primer Gr1

<400> SEQUENCE: 13
aagttgcgra tytgscg         17

<210> SEQ ID NO 14
<211> LENGTH: 788
<212> TYPE: PRT
<213> ORGANISM: Cochliobolus carbonum
<220> FEATURE:
<223> OTHER INFORMATION: Exg1

<400> SEQUENCE: 14

Met Arg Phe Ser Ser Leu Leu Ala Cys Leu Gly Ala Val Gly Ile Gln
 1               5                  10                  15

Ala Ala Ala Ile Pro Phe Gln Arg Arg Val Asp Asn Thr Thr Asp Ser
            20                  25                  30

Gly Ser Leu Asp Ala Ala Gln Ala Ala Ala Ile Val Asp Gly Tyr
        35                  40                  45

Trp Leu Asn Asp Leu Ser Gly Lys Gly Arg Ala Pro Phe Asn Ser Asn
 50                  55                  60

Pro Asn Tyr Lys Val Phe Arg Asn Val Lys Asp Tyr Gly Ala Lys Gly
 65                  70                  75                  80

Asp Gly Val Thr Asp Asp Ser Asp Ala Phe Asn Arg Ala Ile Ser Asp
                85                  90                  95

Gly Ser Arg Cys Gly Pro Trp Val Cys Asp Ser Ser Thr Asp Ser Pro
            100                 105                 110

Ala Val Val Tyr Val Pro Ser Gly Thr Tyr Leu Ile Asn Lys Pro Ile
        115                 120                 125

Ile Phe Tyr Tyr Met Thr Ala Leu Ile Gly Asn Pro Arg Glu Leu Pro
130                 135                 140

Val Leu Lys Ala Ala Ser Ser Leu Gln Ala Leu Ala Leu Ile Asp Gly
145                 150                 155                 160

Ser Pro Tyr Ser Asn Gln Asn Gly Glu Pro Gly Trp Ile Ser Thr Asn
                165                 170                 175

Leu Phe Leu Arg Gln Ile Arg Asn Leu Ile Ile Asp Gly Thr Ala Val
            180                 185                 190

Ala Pro Thr Ser Gly Phe Gln Ala Ile His Trp Pro Ala Ser Gln Ala
        195                 200                 205

-continued

```
Thr Thr Ile Gln Asn Val Lys Ile Arg Met Thr Gln Ala Ser Asn Ser
    210                 215                 220
Val His Ala Gly Ile Phe Val Glu Asn Gly Ser Gly His Met Ala
225                 230                 235                 240
Asp Leu Asp Ile Thr Gly Gly Leu Tyr Gly Met Asn Ile Gly Asn Gln
                    245                 250                 255
Gln Phe Thr Met Arg Asn Val Lys Ile Ser Lys Ala Val Val Gly Ile
                260                 265                 270
Ser Gln Ile Trp Asn Trp Gly Trp Leu Tyr Ser Gly Leu Gln Ile Ser
            275                 280                 285
Asp Cys Gly Thr Ala Phe Ser Met Val Asn Gly Gly Ser Ala Gly Lys
    290                 295                 300
Gln Glu Val Gly Ser Ala Val Ile Ile Asp Ser Glu Ile Thr Asn Cys
305                 310                 315                 320
Gln Lys Phe Val Asp Ser Ala Trp Ser Gln Thr Ser Asn Pro Thr Gly
                325                 330                 335
Ser Gly Gln Leu Val Ile Glu Asn Ile Lys Leu Thr Asn Val Pro Ala
                340                 345                 350
Ala Val Val Ser Asn Gly Ala Thr Val Leu Ala Gly Gly Ser Leu Thr
                355                 360                 365
Ile Gln Thr Trp Gly Gln Gly Asn Lys Tyr Ala Pro Asn Ala Ser Gly
    370                 375                 380
Pro Ser Lys Phe Gln Gly Ala Ile Ser Gly Ala Thr Arg Pro Thr Gly
385                 390                 395                 400
Leu Leu Gln Asn Gly Lys Phe Tyr Ser Lys Ser Lys Pro Gln Tyr Glu
                405                 410                 415
Thr Leu Ser Thr Ser Ser Phe Ile Ser Ala Arg Gly Ala Gly Ala Thr
                420                 425                 430
Gly Asp Gly Val Thr Asp Asp Thr Arg Ala Val Gln Ala Ala Val Thr
            435                 440                 445
Gln Ala Ala Ser Gln Asn Lys Val Leu Phe Glu His Gly Val Tyr
    450                 455                 460
Lys Val Thr Asn Thr Ile Tyr Val Pro Pro Gly Ser Arg Met Val Gly
465                 470                 475                 480
Glu Ile Phe Ser Ala Ile Met Gly Ser Gly Ser Thr Phe Gly Asp Gln
                485                 490                 495
Ala Asn Pro Val Pro Ile Ile Gln Ile Gly Lys Pro Gly Glu Ser Gly
                500                 505                 510
Ser Ile Glu Trp Ser Asp Met Ile Val Gln Thr Gln Gly Ala Thr Pro
        515                 520                 525
Gly Ala Ile Val Ile Gln Tyr Asn Leu Asn Thr Ala Leu Gly Ser Gly
    530                 535                 540
Leu Trp Asp Val His Thr Arg Ile Gly Gly Ala Lys Gly Thr Asn Leu
545                 550                 555                 560
Gln Val Ala Gln Cys Pro Ala Val Leu Gly Gln Val Lys Pro Glu Cys
                565                 570                 575
Phe Ser Ala His Thr Asn Val His Val Thr Lys Gly Ala Asn Gly Ala
                580                 585                 590
Tyr Phe Glu Asn Asn Trp Phe Trp Thr Ala Asp His Asp Leu Asp Asp
            595                 600                 605
Ala Asp Ser Thr Arg Ile Asn Ile Tyr Thr Gly Arg Gly Phe His Val
    610                 615                 620
```

```
Glu Ala Asn Asn Val Trp Ile Trp Ala Asn Gly Ala Glu His His Thr
625                 630                 635                 640

Met Tyr Gln Tyr Gln Phe Asn Ala Ala Gln Asp Ile Phe Ala Gly Tyr
            645                 650                 655

Ile Gln Thr Glu Thr Pro Tyr Phe Gln Pro Thr Pro Ile Ala Pro Leu
                660                 665                 670

Pro Tyr Val Ser Ser Lys Tyr Ser Asp Pro Val Tyr Ser Ser Ser
            675                 680                 685

Gln Thr Ser Ala Trp Gly Leu Arg Leu Leu Asp Ala Lys Asn Val Leu
    690                 695                 700

Ile Tyr Gly Gly Leu Tyr Ser Phe Phe Asp Asn Tyr Asp Val Gly
705                 710                 715                 720

Cys Ser Ser Pro Thr Ala Pro Asn Gly Phe Arg Asp Cys Gln Thr Arg
                725                 730                 735

Ile Leu Ser Ile Glu Gly Ser Thr Ser Val Gln Ala Phe Gly Phe Ser
                740                 745                 750

Glu Val Gly Val Glu Trp Met Val Thr Ala Ala Gly Gln Asp Lys Ala
            755                 760                 765

Asn Trp Lys Asp Asn Leu Ser Val Tyr Pro Thr Thr Ile Gly Tyr Leu
770                 775                 780

Ser Tyr Gly Phe
785

<210> SEQ ID NO 15
<211> LENGTH: 777
<212> TYPE: PRT
<213> ORGANISM: Ampelomyces quisqualis
<220> FEATURE:
<223> OTHER INFORMATION: ExgA

<400> SEQUENCE: 15

Met Leu Ala Phe Ser Ala Gly Ala Phe Leu Leu Thr Leu Arg Val Phe
  1               5                  10                  15

Leu Thr Ala Thr Pro Ser Ala Ala Pro Val Ala Gln Ala Val Glu
             20                  25                  30

Val Pro Gln Ala Gly Ala Ser Gly Tyr Trp Phe Gly Asn Ile Lys Arg
         35                  40                  45

Gln Gly Ile Ala Pro Tyr Asn Glu Asn Pro Ala Ala Tyr Lys Val Phe
     50                  55                  60

Arg Asn Val Lys Leu Leu Gly Ala Lys Gly Asp Gly Val Thr Asp Asp
 65                  70                  75                  80

Thr Ala Ile Asn Ala Ala Ile Ala Asp Gly Asn Arg Cys Gly Gln
             85                  90                  95

Gly Cys Asp Ser Thr Thr Thr Ser Pro Ala Ile Ile Tyr Phe Pro Ala
                100                 105                 110

Gly Thr Tyr Leu Ile Ser Glu Pro Ile Ile Gln Tyr Tyr Thr Gln
            115                 120                 125

Phe Val Gly Asp Ala Thr Asn Pro Pro Thr Leu Lys Ala Lys Asp Thr
130                 135                 140

Phe Glu Gly Met Gly Leu Ile Asp Ala Asp Pro Tyr Ile Pro Gly Gly
145                 150                 155                 160

Asp Gly Ala Asn Trp Tyr Thr Asn Gln Asn Phe Tyr Arg Gln Ile
                165                 170                 175

Arg Asn Phe Val Ile Asp Ile Lys Asp Thr Lys Ala Ala Ala Gly Ile
                180                 185                 190
```

-continued

```
His Trp Gln Val Ser Gln Ala Thr Ser Leu Gln Asn Ile Arg Phe Glu
            195                 200                 205
Met Ala Thr Gly Glu Ala Gly Ala Asn Gln Lys Gly Ile Phe Gln Asp
            210                 215                 220
Asn Gly Ser Gly Gly Phe Met Ser Asp Leu Val Phe Asn Gly Gly Ala
225                 230                 235                 240
Ile Gly Ala Phe Leu Gly Ser Gln Gln Phe Thr Thr Arg Asn Met Thr
                245                 250                 255
Phe Asn Asn Cys Gly Thr Ala Ile Phe Met Asn Trp Asn Trp Leu Trp
                260                 265                 270
Thr Leu Lys Ser Ile Phe Ile Asn Asp Cys Lys Leu Gly Leu Asp Met
            275                 280                 285
Ala Asn Ser Pro Asp Asn Gln Thr Val Gly Ser Val Leu Leu Leu Asp
            290                 295                 300
Ser Lys Phe Thr Asn Thr Pro Ile Gly Ile Asn Ser Ser Phe Thr Gln
305                 310                 315                 320
Asp Ser Val Pro His Thr Gly Gly Thr Leu Ile Ile Asp Asn Val Asp
                325                 330                 335
Phe Glu Gly Ser Asn Val Ala Val Gln Asn Val Ala Gly Glu Thr Leu
                340                 345                 350
Leu Ala Gly Lys Ser Lys Val Ala Thr Trp Ala Gln Gly Asn Ala Met
            355                 360                 365
Ala Ala Gly Gln Ala Gln Ala Gly Arg Val Gln Gly Asp Val Asn Asn
            370                 375                 380
Pro Pro Thr Lys Pro Gln Ser Leu Leu Gly Glu Asn Gly Trp Phe Glu
385                 390                 395                 400
Arg Ser Lys Pro Gln Tyr Glu Asn Ile Asp Val Ser Lys Phe Val Ser
                405                 410                 415
Leu Lys Asp Ala Gly Ala Val Gly Asp Gly Val Thr Asp Thr Ala
            420                 425                 430
Met Ile Gln Lys Ala Ile Asp Gly Leu Gln Asp Gly Gln Ile Leu His
            435                 440                 445
Ala Asp His Gly Ala Tyr Leu Ile Thr Lys Thr Ile Glu Ile Pro Ala
450                 455                 460
Glu Lys Asn Ile Lys Ile Val Gly Glu Ile Tyr Thr Met Phe Phe Ile
465                 470                 475                 480
Thr Gly Lys Phe Phe Gly Asn Met Asp Asp Pro Gln Pro Gly Phe Arg
                485                 490                 495
Val Gly Lys Lys Ser Gly Asp Lys Gly Thr Phe Glu Met Ser Asp Ala
            500                 505                 510
Ile Ile Ser Thr Gln Gly Pro Ala Pro Gly Ile Leu Met Glu Trp
            515                 520                 525
Asn Ile Asn Ala Glu Ala Gly Lys Ala Gly Leu Trp Asp Val His Phe
530                 535                 540
Arg Val Gly Gly Phe Ala Gly Thr Asn Leu Gln Ser Ser Asn Cys Lys
545                 550                 555                 560
Lys Asn Pro Asp Thr Glu His Pro Asn Glu Glu Cys Ile Gly Ser
                565                 570                 575
Phe Met Gln Leu His Ile Thr Lys Ser Ser Ser Gly Tyr Phe Glu Asn
            580                 585                 590
Val Trp Leu Trp Thr Ala Asp His Glu Leu Asp Gln Pro Asp His Ala
            595                 600                 605
Gln Ile Asp Ile Tyr Asn Gly Arg Gly Met Leu Val Glu Ser Gln Gly
```

```
            610                 615                 620
Pro Val Trp Leu Val Gly Thr Ala Ser Glu His Ser Gln Leu Ser Gln
625                 630                 635                 640

Tyr Gln Phe Gln Gly Ala Lys Asp Ile Trp Tyr Gly Ala Ile Gln Thr
                645                 650                 655

Glu Thr Pro Tyr Tyr Gln Pro Asn Pro Lys Ala Asn Val Pro Phe Lys
            660                 665                 670

Lys Asn Asp Lys Phe Ser Asp Pro Asp Met Ser Asn Thr Thr Ser Ala
        675                 680                 685

Trp Ala Val Arg Ile Ile Asp Ser Ser Ile Trp Asn Tyr Gly Ala
    690                 695                 700

Gly Thr Tyr Ser Phe Phe Asp Asn Tyr Ser Gln Lys Cys Val Val Gly
705                 710                 715                 720

Gln Asn Cys Gln Glu His Ile Asn Glu Ile Glu Asn Ser Arg Asn Val
                725                 730                 735

Asn Ile Phe Gly Leu Ser Thr Lys Ala Ser Val Asn Met Ile Ser Ser
            740                 745                 750

Gly Gly Val Gly Leu Leu Lys Asp Glu Asp Asn Arg Ser Asn Phe Cys
        755                 760                 765

Ala Thr Leu Gly Ile Phe Ala Gln Ala
    770                 775
```

<210> SEQ ID NO 16
<211> LENGTH: 1032
<212> TYPE: PRT
<213> ORGANISM: Trichoderma harzianum
<220> FEATURE:
<223> OTHER INFORMATION: Trexo

<400> SEQUENCE: 16

```
Met Gly Phe Ile Arg Ser Ala Val Leu Ser Ala Leu Thr Phe Ala Ala
 1               5                  10                  15

Ala Cys Arg Gly Leu Ala Thr Pro Gly Ser Glu Ala Glu Pro Ser Val
            20                  25                  30

Glu Lys Arg Ala Ser Ser Tyr Trp Tyr Glu Asn Ile Ala His Gln Gly
        35                  40                  45

Ile Ala Pro Phe Ala Pro Ser Asn Tyr Thr Val Phe Arg Asn Val Lys
50                  55                  60

Asp Tyr Gly Ala Lys Gly Asp Gly Val Thr Asp Thr Ala Ala Ile
65                  70                  75              80

Asn Asn Ala Ile Leu Ser Gly Gly Arg Cys Gly Arg Leu Cys Thr Ser
                85                  90                  95

Ser Thr Leu Thr Pro Ala Val Val Tyr Phe Pro Ala Gly Thr Tyr Val
            100                 105                 110

Ile Ser Thr Pro Ile Ile Asp Gln Tyr Tyr Thr Asn Ile Ile Gly Asp
        115                 120                 125

Pro Thr Asn Leu Pro Thr Ile Lys Ala Thr Ala Gly Phe Ser Gly Ile
    130                 135                 140

Ala Leu Ile Asp Gly Asp Thr Tyr Tyr Gly Asp Asn Asn Pro Asn Asp
145                 150                 155                 160

Pro Asn Trp Ile Ser Thr Asn Val Phe Tyr Arg Gln Val Arg Asn Phe
                165                 170                 175

Lys Leu Asp Met Thr Ser Ile Pro Thr Ser Ala Pro Lys Ile Tyr Gly
            180                 185                 190

Ile His Trp Pro Thr Ala Gln Ala Thr Ser Leu Gln Asn Ile Gln Ile
```

-continued

```
                195                 200                 205
Thr Met Ser Thr Ala Ser Gly Asn Ser Gln Val Gly Leu Phe Ile Glu
    210                 215                 220
Asn Gly Ser Ala Gly Phe Leu Thr Asp Met Thr Phe Asn Gly Gly Leu
225                 230                 235                 240
Ile Gly Ala Ala Ile Gly Asn Gln Gln Tyr Thr Met Arg Asn Leu Val
                245                 250                 255
Phe Asn Asn Cys Ala Gln Pro Leu Ser Ala Ser Ile Gly Ser Gly
            260                 265                 270
Phe Thr Arg Ala Ile Ser Ile Asn Asn Cys Gly Leu Gly Ile Asp Met
            275                 280                 285
Thr Ala Ala Glu Ser Ile Thr Leu Ile Asp Ser Ser Ile Ser Gly Thr
    290                 295                 300
Pro Val Gly Ile Lys Thr Ser Phe Arg Arg Asn Gln Ser Pro Ala Thr
305                 310                 315                 320
Ser Asn Ser Leu Ile Val Glu Asn Leu Ser Leu Asn Asn Val Pro Val
                325                 330                 335
Ala Ile Gln Ser Ser Gly Ser Thr Ile Leu Ala Gly Gly Thr Thr
            340                 345                 350
Thr Ile Ala Ala Trp Gly Gln Gly His Gln Tyr Thr Pro Asn Gly Pro
    355                 360                 365
Thr Thr Phe Gln Gly Ser Ile Thr Pro Asn Ser Arg Pro Ser Ser Leu
    370                 375                 380
Leu Ser Gly Ser Asn Tyr Tyr Thr Arg Ser Lys Pro Gln Tyr Glu Thr
385                 390                 395                 400
Leu Pro Val Ser Ser Phe Arg Ser Val Arg Ser Ala Gly Ala Thr Gly
                405                 410                 415
Asn Ala Val Thr Asp Asp Thr Ala Ala Leu Gln Ser Val Ile Asn Ser
                420                 425                 430
Ala Thr Ala Cys Gly Gln Ile Val Tyr Phe Asp Ala Gly Ile Tyr Arg
            435                 440                 445
Ile Thr Ser Thr Leu Ser Ile Pro Pro Gly Ala Lys Ile Val Gly Glu
    450                 455                 460
Glu Tyr Pro Ile Ile Met Ser Ser Gly Ser Phe Phe Asn Asp Gln Ser
465                 470                 475                 480
Asn Pro Lys Pro Val Val Gln Val Gly Thr Pro Gly Gln Thr Gly Gln
                485                 490                 495
Val Glu Trp Ser Asp Met Ile Val Ser Thr Gln Gly Thr Gln Ala Gly
                500                 505                 510
Ala Val Leu Ile Glu Trp Asn Leu Ala Thr Ser Gly Thr Pro Ser Gly
            515                 520                 525
Met Trp Asp Val His Thr Arg Ile Gly Gly Phe Lys Gly Ser Asn Leu
    530                 535                 540
Gln Val Ala Gln Cys Pro Val Thr Ala Ser Ser Thr Val Asn Thr
545                 550                 555                 560
Ala Cys Ile Gly Ala Tyr Met Ser Met His Ile Thr Ala Ser Ala Ser
            565                 570                 575
Asn Leu Tyr Met Glu Asn Asn Trp Leu Trp Thr Ala Asp His Asp Ile
            580                 585                 590
Asp Asp Ser Ser Asn Thr Gln Ile Thr Ile Phe Ser Gly Arg Gly Leu
        595                 600                 605
Tyr Val Glu Ser Thr Ala Gly Thr Phe Trp Phe Val Gly Thr Ala Val
    610                 615                 620
```

-continued

Glu His His Thr Leu Tyr Gln Tyr Gln Phe Ala Asn Thr Gln Asn Ile
625                 630                 635                 640

Tyr Ala Gly Val Ile Gln Thr Glu Thr Pro Tyr Tyr Gln Pro Asn Pro
            645                 650                 655

Asp Ala Pro Thr Pro Phe Asn Val Asn Thr Ala Leu Asn Asp Pro Asn
        660                 665                 670

Phe Ala Thr Ser Cys Ser Gly Ser Ser Gly Arg Cys Ala Glu Ala Trp
    675                 680                 685

Gly Leu Arg Ile Val Ser Ser Gln Asn Ile Leu Ile Tyr Ala Ala Gly
690                 695                 700

Leu Tyr Ser Phe Phe Glu Asn Asn Asp Gly Asn Thr Gly Cys Asp Val
705                 710                 715                 720

Ala Leu Gly Pro Glu Asn Cys Gln Asn Asn Ile Phe Asp Leu Glu Gly
            725                 730                 735

Thr Leu Thr Asn Ile Asn Val Tyr Asn Leu Gly Thr Val Gly Val Val
        740                 745                 750

Asn Gln Ile Thr Gln Asn Gly Asn Val Leu Ala Thr Ser Ser Ser Asn
    755                 760                 765

Val Asn Ala Phe Ala Asp Val Ile Ala Leu Phe Arg Leu Ala Ser Gly
770                 775                 780

Ser Gly Gly Val Thr Pro Pro Ser Ser Thr Thr Lys Ala Gln Ser
785                 790                 795                 800

Thr Thr Phe Ser Thr Ile Ile Thr Ser Ser Pro Pro Lys Gln Thr Gly
            805                 810                 815

Trp Asn Phe Leu Gly Cys Tyr Ser Asp Asn Val Asn Gly Arg Thr Leu
        820                 825                 830

Ala Asn Gln Val Gln Val Ala Gly Gly Ala Ser Ala Met Ser Ile Glu
    835                 840                 845

Ala Cys Glu Thr Ala Ser Glu Ser Ala Gly Tyr Thr Ile Ala Gly Val
850                 855                 860

Glu Tyr Ser Gly Glu Cys Trp Cys Asp Thr Lys Phe Gln Asn Gly Gly
865                 870                 875                 880

Gly Pro Ala Ser Asp Gly Ser Ala Gln Cys Thr Met Thr Cys Ser Gly
            885                 890                 895

Ala Pro Gln Glu Thr Cys Gly Gly Pro Asn Arg Leu Asp Val Tyr Ser
        900                 905                 910

Leu Ala Thr Ala Thr Gly Ser Ala Ser Pro Pro Ala Ala Thr Gly Trp
    915                 920                 925

Asn Phe Arg Gly Cys Tyr Thr Asp Ser Val Asn Ala Arg Ala Leu Ile
930                 935                 940

Ala Glu Ser Val Pro Asn Gly Pro Ser Ser Met Thr Ile Glu Ala Cys
945                 950                 955                 960

Gln Ser Val Cys Lys Gly Leu Gly Tyr Thr Leu Ala Gly Leu Glu Tyr
            965                 970                 975

Ala Asp Glu Cys Tyr Cys Gly Asn Ser Leu Ala Asn Gly Ala Thr Ile
        980                 985                 990

Ala Pro Asp Gly Asn Ala Gly Cys Asn Met Asn Cys Ala Gly Asn Ala
    995                 1000                1005

Ala Glu Thr Cys Gly Gly Pro Asn Arg Leu Asp Ile Tyr Ser Tyr Gly
    1010                1015                1020

Gln Ala Asn Gly Thr Gln Pro Leu
1025                1030

```
<210> SEQ ID NO 17
<211> LENGTH: 762
<212> TYPE: PRT
<213> ORGANISM: Trichoderma harzianum
<220> FEATURE:
<223> OTHER INFORMATION: Bgn13.1

<400> SEQUENCE: 17
```

| | | | | | | | | | | | | | | | |
|---|---|---|---|---|---|---|---|---|---|---|---|---|---|---|---|
| Met | Leu | Lys | Leu | Thr | Ala | Leu | Val | Ala | Leu | Leu | Gly | Ala | Ala | Ser | |
| 1 | | | | 5 | | | | | 10 | | | | | 15 | |
| Ala | Thr | Pro | Thr | Pro | Ser | Pro | Pro | Ala | Ser | Asp | Glu | Gly | Ile | Thr | Lys |
| | | | 20 | | | | | 25 | | | | | 30 | | |
| Arg | Ala | Thr | Ser | Phe | Tyr | Tyr | Pro | Asn | Met | Asp | His | Val | Asn | Ala | Pro |
| | | 35 | | | | | 40 | | | | | 45 | | | |
| Arg | Gly | Phe | Ala | Pro | Asp | Leu | Asp | Gly | Asp | Phe | Asn | Tyr | Pro | Ile | Tyr |
| | 50 | | | | | 55 | | | | | 60 | | | | |
| Gln | Thr | Val | Asn | Ala | Gly | Asp | Gly | Asn | Ala | Leu | Gln | Asn | Ala | Ile | Thr |
| 65 | | | | | 70 | | | | | 75 | | | | | 80 |
| Thr | Asp | Gly | Lys | Gly | Gly | Ser | Arg | His | Pro | Gln | Trp | Phe | Ala | Ser | Gln |
| | | | | 85 | | | | | 90 | | | | | 95 | |
| Pro | Arg | Val | Val | Tyr | Ile | Pro | Pro | Gly | Thr | Tyr | Thr | Ile | Ser | Lys | Thr |
| | | | 100 | | | | | 105 | | | | | 110 | | |
| Leu | Arg | Phe | Asn | Thr | Asp | Thr | Ile | Leu | Met | Gly | Asp | Pro | Thr | Asn | Pro |
| | | 115 | | | | | 120 | | | | | 125 | | | |
| Pro | Ile | Ile | Lys | Ala | Ala | Ala | Gly | Phe | Ser | Gly | Asp | Gln | Thr | Leu | Ile |
| | 130 | | | | | 135 | | | | | 140 | | | | |
| Ser | Ala | Gln | Asp | Pro | Ser | Thr | Asn | Glu | Lys | Gly | Glu | Leu | Ser | Phe | Ala |
| 145 | | | | | 150 | | | | | 155 | | | | | 160 |
| Val | Ala | Ile | Lys | Asn | Val | Val | Leu | Asp | Thr | Thr | Ala | Ile | Pro | Gly | Gly |
| | | | | 165 | | | | | 170 | | | | | 175 | |
| Asn | Ser | Phe | Thr | Ala | Leu | Trp | Trp | Gly | Val | Ala | Gln | Ala | Ala | His | Leu |
| | | | 180 | | | | | 185 | | | | | 190 | | |
| Gln | Asn | Val | Arg | Ile | Thr | Met | Ser | Ser | Ser | Ser | Gly | Gly | Asn | Gly | His |
| | | 195 | | | | | 200 | | | | | 205 | | | |
| Thr | Gly | Ile | Arg | Met | Gly | Arg | Gly | Ser | Thr | Leu | Gly | Leu | Ala | Asp | Val |
| | 210 | | | | | 215 | | | | | 220 | | | | |
| Arg | Val | Glu | Arg | Gly | Gln | Asn | Gly | Ile | Trp | Ile | Asp | Gly | His | Gln | Gln |
| 225 | | | | | 230 | | | | | 235 | | | | | 240 |
| Ala | Ser | Phe | His | Asn | Ile | Tyr | Phe | Phe | Gln | Asn | Thr | Ile | Gly | Met | Leu |
| | | | | 245 | | | | | 250 | | | | | 255 | |
| Ile | Ser | Ser | Gly | Asn | Thr | Phe | Ser | Ile | Phe | Ser | Ser | Thr | Phe | Asp | Thr |
| | | | 260 | | | | | 265 | | | | | 270 | | |
| Cys | Gly | Thr | Ala | Phe | Pro | Thr | Leu | Ala | Gly | Ser | Pro | Trp | Ile | Ala | Leu |
| | | 275 | | | | | 280 | | | | | 285 | | | |
| Ile | Asp | Ala | Lys | Ser | Ile | Asn | Ser | Gly | Val | Thr | Phe | Thr | Thr | Asn | Gln |
| | 290 | | | | | 295 | | | | | 300 | | | | |
| Phe | Pro | Ser | Phe | Met | Ile | Glu | Asn | Leu | Thr | Lys | Asp | Asn | Gly | Thr | Pro |
| 305 | | | | | 310 | | | | | 315 | | | | | 320 |
| Val | Val | Val | Val | Arg | Gly | Ser | Thr | Leu | Val | Gly | Ala | Ser | Ser | His | Val |
| | | | | 325 | | | | | 330 | | | | | 335 | |
| Asn | Thr | Tyr | Ser | Tyr | Gly | Asn | Thr | Val | Gly | Arg | Asn | Pro | Thr | Tyr | Gly |
| | | | 340 | | | | | 345 | | | | | 350 | | |
| Asp | Val | Thr | Ser | Ser | Asn | Thr | Arg | Pro | Ser | Ala | Leu | Ala | Pro | Gly | Gly |
| | | 355 | | | | | 360 | | | | | 365 | | | |

-continued

```
Arg Tyr Pro Tyr Val Ala Pro Thr Tyr Gly Asp Leu Pro Ile Ser
    370                 375                 380

Ser Phe Leu Asn Val Lys Asp Pro Ala Gln Asn Gly Asn Arg Gln Val
385                 390                 395                 400

Lys Gly Asp Asn Thr Ile Asn Glu Ala Asp Thr Leu Asn Ala Ile Leu
                405                 410                 415

Glu Leu Ala Ala Ser Gln Asn Lys Val Ala Tyr Phe Pro Phe Gly Lys
            420                 425                 430

Tyr Arg Val Asp Ser Thr Leu Phe Ile Pro Lys Gly Ser Arg Ile Val
                435                 440                 445

Gly Glu Ala Trp Ala Thr Ile Thr Gly Asn Gly Asn Phe Phe Lys Asn
450                 455                 460

Glu Asn Ser Pro Gln Pro Val Val Ser Val Gly Arg Ala Gly Asp Val
465                 470                 475                 480

Gly Ile Ala Gln Leu Gln Asp Leu Arg Val Thr Thr Asn Asp Val Leu
                485                 490                 495

Pro Gly Ala Ile Leu Val Gln Phe Asn Met Ala Gly Asn Asn Pro Gly
            500                 505                 510

Asp Val Ala Leu Trp Asn Ser Leu Val Thr Val Gly Thr Arg Gly
        515                 520                 525

Ala Gln Ala Leu Ala Asn Ala Cys Thr Asn Asn Ser Asn Glu Cys Lys
530                 535                 540

Gly Ala Phe Ile Gly Ile His Val Ala Lys Gly Ser Ser Pro Tyr Ile
545                 550                 555                 560

Gln Asn Val Trp Glu Leu Gly Leu Arg Asp His Ile Ala Glu Asn Phe
                565                 570                 575

Ser Gly Gly Thr Ser His Arg Arg Glu Arg Trp Asn Phe Gly Pro Ile
            580                 585                 590

Arg Arg Asn Ala Thr Cys Leu Tyr Pro Ile Gly Ser Gly His Trp Trp
        595                 600                 605

Leu Tyr Gln Leu Asn Leu His Asn Ala Ala Asn Val Val Ser Leu
610                 615                 620

Leu Gln Ala Glu Thr Asn Tyr His Gln Gly Ala Asn Thr Gln Gln Ile
625                 630                 635                 640

Pro Pro Ala Pro Trp Val Ala Asn Val Gly Thr Trp Gly Asp Pro Asp
                645                 650                 655

Phe Ser Trp Cys Asn Gly Gly Asp Lys Arg Cys Arg Met Gly Pro Ala
            660                 665                 670

Asn Phe Ile Asn Gly Gly Ser Asn Ile Tyr Thr Tyr Ala Ser Ala Ala
        675                 680                 685

Trp Ala Phe Phe Ser Gly Pro Gly Gln Gly Cys Ala Gln Phe Glu Cys
690                 695                 700

Gln Gln Thr Ile His Trp Ile Ala Ser Thr Pro Ser Asn Leu Gln Ala
705                 710                 715                 720

Phe Gly Leu Cys Ser Lys Asp Ser Val Asn Thr Leu Arg Leu Gly Asp
                725                 730                 735

Gly Thr Phe Ile Asn Thr Gln Asn Gly Tyr Thr Gly Gly Trp Thr Pro
            740                 745                 750

Gly Gly Gly Asp Val Ala Arg Tyr Thr Thr
        755                 760
```

<210> SEQ ID NO 18
<211> LENGTH: 45
<212> TYPE: PRT

```
<213> ORGANISM: Bacteriophage phi-29
<220> FEATURE:
<223> OTHER INFORMATION: Phi-29

<400> SEQUENCE: 18

Ser Val Lys Thr Tyr Gly Ala Lys Gly Asp Gly Val Thr Asp Asp Ile
 1               5                  10                  15
Arg Ala Phe Glu Lys Ala Ile Glu Ser Gly Phe Pro Val Tyr Val Pro
                20                  25                  30
Tyr Gly Thr Phe Met Val Ser Arg Gly Ile Lys Leu Pro
            35                  40                  45

<210> SEQ ID NO 19
<211> LENGTH: 60
<212> TYPE: PRT
<213> ORGANISM: Azotobacter vinelandii
<220> FEATURE:
<223> OTHER INFORMATION: AlgE7

<400> SEQUENCE: 19

Gly Ala Lys Gly Asp Gly Lys Thr Asp Asp Thr Asp Ala Ile Gln Ala
 1               5                  10                  15

Ala Ile Asp Ala Ala His Lys Ala Gly Gly Thr Val Tyr Leu Pro
                20                  25                  30

Ser Gly Glu Tyr Arg Val Ser Gly Gly Asp Glu Ala Ser Asp Gly Ala
            35                  40                  45

Leu Ile Ile Lys Ser Asn Val Tyr Ile Val Gly Ala
        50                  55                  60

<210> SEQ ID NO 20
<211> LENGTH: 54
<212> TYPE: PRT
<213> ORGANISM: Bacteriophage K1F
<220> FEATURE:
<223> OTHER INFORMATION: Endo-N

<400> SEQUENCE: 20

Ala Arg Gly Trp Gly Ala Lys Gly Asp Gly Val Thr Asp Asp Thr Ala
 1               5                  10                  15

Ala Leu Thr Ser Ala Leu Asn Asp Thr Pro Val Gly Gln Lys Ile Asn
                20                  25                  30

Gly Asn Gly Lys Thr Tyr Lys Val Thr Ser Leu Pro Asp Ile Ser Arg
            35                  40                  45

Phe Ile Asn Thr Arg Phe
        50

<210> SEQ ID NO 21
<211> LENGTH: 54
<212> TYPE: PRT
<213> ORGANISM: Arabidopsis thaliana
<220> FEATURE:
<223> OTHER INFORMATION: Exopg

<400> SEQUENCE: 21

Gly Ala Ala Val Asp Val Lys Ser Gly Ala Lys Gly Asp Gly Lys
 1               5                  10                  15

Thr Asp Asp Ser Ala Ala Phe Ala Ala Ala Trp Lys Glu Ala Cys Ala
                20                  25                  30

Ala Gly Ser Thr Ile Thr Val Pro Lys Gly Glu Tyr Met Val Glu Ser
            35                  40                  45

Leu Glu Phe Lys Gly Pro
        50
```

```
<210> SEQ ID NO 22
<211> LENGTH: 7
<212> TYPE: PRT
<213> ORGANISM: Coniothyrium minitans
<220> FEATURE:
<223> OTHER INFORMATION: Domain within cbeg1
<220> FEATURE:
<221> NAME/KEY: misc_feature
<222> LOCATION: (4)..(4)
<223> OTHER INFORMATION: Xaa is a valine, serine or lysine

<400> SEQUENCE: 22

Gly Asp Gly Xaa Thr Asp Asp
 1               5

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: universal
      24 base M13 forward primer

<400> SEQUENCE: 23
cgccagggtt ttcccagtca cgac                                            24

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: 24 base
      reverse primer

<400> SEQUENCE: 24
agcggataac aatttcacac agga                                            24
```